United States Patent [19]
Bellamkonda et al.

[11] Patent Number: 5,834,029
[45] Date of Patent: Nov. 10, 1998

[54] NERVE GUIDANCE CHANNEL CONTAINING BIOARTIFICIAL THREE-DIMENSIONAL HYDROGEL EXTRACELLULAR MATRIX DERIVATIZED WITH CELL ADHESIVE PEPTIDE FRAGMENT

[75] Inventors: Ravi Bellamkonda, Boston, Mass.; John P. Ranieri, Lausanne; Patrick Aebischer, Lutry, both of Switzerland

[73] Assignee: CytoTherapeutics, Inc., Lincoln, R.I.

[21] Appl. No.: 280,646

[22] Filed: Jul. 20, 1994

[51] Int. Cl.$^6$ .......................... A61K 35/30; C12N 11/10; C12N 5/00; A61B 17/08

[52] U.S. Cl. ........................ 424/570; 424/93.7; 435/177; 435/178; 435/368; 435/395; 435/397; 435/402; 530/326; 530/328; 530/329; 530/402; 606/152

[58] Field of Search .................................. 435/174, 177, 435/178, 240.243, 368, 395, 397, 402; 606/152; 530/326, 327, 328, 329, 330, 402; 424/570

[56] References Cited

U.S. PATENT DOCUMENTS

| | | | |
|---|---|---|---|
| 4,495,288 | 1/1985 | Jarvis, Jr. et al. | 435/241 |
| 4,829,000 | 5/1989 | Kleinman et al. | 435/240.3 |
| 4,963,146 | 10/1990 | Li | 606/152 |
| 5,011,486 | 4/1991 | Aebischer et al. | 606/152 |
| 5,019,087 | 5/1991 | Nichols | 606/152 |
| 5,026,381 | 6/1991 | Li | 606/623 |
| 5,030,225 | 7/1991 | Aebischer et al. | 606/152 |
| 5,068,224 | 11/1991 | Fryklund et al. | 514/21 |
| 5,081,031 | 1/1992 | Tsilibary et al. | 435/402 |
| 5,082,670 | 1/1992 | Gage et al. | 424/520 |
| 5,092,871 | 3/1992 | Aebischer et al. | 606/152 |
| 5,106,627 | 4/1992 | Aebischer et al. | 424/424 |
| 5,147,797 | 9/1992 | McCarthy et al. | 435/398 |
| 5,156,844 | 10/1992 | Aebischer et al. | 424/424 |
| 5,158,881 | 10/1992 | Aebisher et al. | 435/182 |
| 5,166,187 | 11/1992 | Collombel et al. | 514/21 |
| 5,171,271 | 12/1992 | Furcht et al. | 623/11 |
| 5,202,120 | 4/1993 | Silver et al. | 424/930 |
| 5,250,414 | 10/1993 | Schwab et al. | 435/7.72 |
| 5,279,966 | 1/1994 | Jessell et al. | 435/320.1 |
| 5,283,187 | 2/1994 | Aebischer et al. | 435/182 |
| 5,284,761 | 2/1994 | Aebischer et al. | 435/182 |
| 5,294,551 | 3/1994 | Fucht et al. | 435/402 |
| 5,330,911 | 7/1994 | Hubbell et al. | 435/240.243 |

FOREIGN PATENT DOCUMENTS

| | | |
|---|---|---|
| WO 90/05552 | 5/1990 | WIPO . |
| WO 92/03536 | 3/1992 | WIPO . |
| WO 92/19195 | 11/1992 | WIPO . |
| WO 93/01275 | 1/1993 | WIPO . |
| WO 93/10722 | 6/1993 | WIPO . |
| WO 93/11781 | 6/1993 | WIPO . |
| WO 93/14790 | 8/1993 | WIPO . |

OTHER PUBLICATIONS

Aebischer, Patrick, et al., "Regeneration of Transected Sciatic Nerves Through Semi–Permeable Nerve Guidance Channels," *Trans. Am. Soc. Artif. Intern. Organs*, 32, pp. 474–477 (1986).

Aebischer, Patrick, et al., "Plezoelectric [sic: Piezoelectric] guidance channels enhance regeneration in the mouse sciatic nerve after axotomy," *Brain Research*, 436, pp. 165–168 (1987).

Aebischer, P., et al., "Blind–ended semipermeable guidance channels support peripheral nerve regeneration in the absence of a distal nerve stump," *Brain Research*, 454, pp. 179–187 (1988).

Aebischer, P., et al., "The use of a semi–permeable tube as a guidance channel for a transected rabbit optic nerve," *Progress in Brain Research* (Gash and Sladek, eds.), 78, pp. 599–603 (1988).

Aebischer, P., et al., "Basic Fibroblast Growth Factor Released From Synthetic Guidance Channels Facilitates Peripheral Nerve Regeneration Across Long Nerve Gaps," *Journal of Neuroscience Research*, 23, pp. 282–289 (1989).

Aebischer, Patrick, et al., "The Morphology of Regenerating Peripheral Nerves is Modulated by the Surface Microgeometry of Polymeric Guidance Channels," *Brain Research*, 531, pp. 211–218 (1990).

Aebischer, P., et al., "Macroencapsulation of Dopamine–Secreting Cells By Coextrusion With an Organic Polymer Solution," *Biomaterials*, 12, pp. 50–56 (1991).

Alberts, et al., "Ch 16: The Cytoskeleton," *Molecular Biology of the Cell 3rd Ed.* (Garland Publishing Inc.), pp. 802–824.

Aulthouse, Amy Lynn, et al., "Expression of the Human Chondrocyte Phenotype In Vitro," *In Vitro Cellular & Developmental Biology*, 25, pp. 659–668 (1989).

(List continued on next page.)

*Primary Examiner*—David M. Naff
*Attorney, Agent, or Firm*—Ivor R. Elrifi; Mintz Levin

[57] ABSTRACT

A bioartificial three-dimensional hydrogel extracellular matrix derivatized with a cell adhesive peptide fragment is provided for use in tissue regeneration or replacement. The choice of adhesive peptide fragment depends on the desired target cell type. Cartilage or tendon can be regenerated by implanting a matrix containing adhesive peptide fragments that favor chondrocyte invasion. The matrix can be pre-seeded with cells, and tissue can be reconstituted in vitro and then implanted. A cell-seeded matrix can be encapsulated in a semi-permeable membrane to form a bioartificial organ. An agarose hydrogel matrix having an agarose concentration of 0.5–1.25% (w/v) and an average gel pore radius between 120 nm and 290 nm is preferred. The peptide fragment preferably contains the sequence, ArgGlyAsp or TyrIleGlySerArg or IleLysValAlaVal, and is covalently immobilized to the matrix. A nerve guidance channel for use in regenerating severed nerve is prepared containing a tubular semi-permeable membrane having openings adapted to receive the ends of a severed nerve, and an inner lumen containing the matrix having an adhesive peptide fragment through which the nerve can regenerate.

9 Claims, 7 Drawing Sheets

OTHER PUBLICATIONS

Aumailley, Monique, et al., "Cell Attachment Properties of Collagen Type VI and Arg–Gly–Asp Dependent Binding to its α2 (VI) and α3(VI) Chains," *Exper. Cell Research*, 181, pp. 463–474 (1989).

Azzi, Georges, et al., "Immunolocalisation of Extracellular Matrix Macromolecules in the Rat Spinal Cord," *Matrix*, 9, pp. 479–485 (1989).

Baron–Van Evercooren, Anne, et al., "Nerve Growth Factor, Laminin, and Fibronectin Promote Nuerite Growth in Human Fetal Sensory Ganglia Cultures," *J. Neuroscience Research*, 8, pp. 179–193 (1982).

Baron–Van Evercooren, A., et al., "Schwann Cell Differentiation in vitro: Extracellular Matrix Deposition and Interaction," *Dev. Neurosci.*, 8, pp. 182–196 (1986).

Benya, Paul D., and Joy D. Shaffer, "Dedifferentiated Chondrocytes Reexpress the Differentiated Collagen Phenotype When Cultured in Agarose Gels," *Cell*, 30, pp. 215–224 (1982).

Blau, Helen M., et al., "Myoblasts in Pattern Formation and Gene Therapy," *Trends in Genetics*, 9, pp. 269–274 (1993).

Cabasso, I., "Hollow–Fiber Membranes," *Encyclopedia of Chemical Technology* (Kirk–Othmer, ed.), 12, pp. 492–517 (1980).

Calof, Anne L., et al., "Domain–Specific Activation of Neuronal Migration and Neurite Outgrowth–Promoting Activities of Laminin," *Neuron*, 13, pp. 117–130 (1994).

Carbonetto, Salvatore, "Ch. 15: Laminin Receptors: From PC12 Cells to PNS," *Brain Repair* (Björklund, Aguayo, and Ottoson, eds.), pp. 185–197 (1990).

Celtrix Laboratories, "Vitrogen 100®: Purified Collagen for Cell Culture and Biochemistry" (Product Information Memorandum), Celtrix Laboratories, Palo Alto, CA (1991).

Chiu, Arlene Y., and Joshua R. Sanes, "Development of Basal Lamina On Synaptic and Extrasynaptic Portions of Embryonic Rat Muscle," *Development Biology*, 103, pp. 456–467 (1984).

Chu, C.H., and A.M. Tolkovsky, "Alternative Adrenal Chromaffin Cell Fates Induced by Basic Fibroblast Growth Factor or Cyclic AMP In Vitro Depend on a Collaboration With The Growth Substrate," *Neuroscience*, 59, pp. 43–54 (1994).

Collaborative Research Incorporated, "CR–LAMININ and CR–ANTI–LAMININ" (Product Information Memorandum), Collaborative Research, Inc., Bedford, MA (1987).

Collaborative Research Incorporated, "Basement Membrane Matrigel™" (Product Specification Sheet), Collaborative Research, Inc., Bedford, MA (1991).

Crossin, Kathryn L., et al., "Expression Sequences of Cell Adhesion Molecules," *Proc. Natl. Acad. Sci USA*, 82, pp. 6942–6946 (1985).

Daniloff, Joanne K., et al., "Differential Distribution of Cell Adhesion Molecules During Histogenesis of the Chick Nervous System," *J. Neuroscience*, 6, pp. 739–758 (1986).

de Bruine, Adriaan P., et al., "Extracellular Matrix Components Induce Endocrine Differentiation In Vitro in NCI–H716 Cells," *American Journal of Pathology*, 142, pp. 773–782 (1993).

Dedhar, Shoukat, et al., "A Cell Surface Receptor Complex for Collagen Type I Recognizes the Arg–Gly–Asp Sequence," *J. Cell Biol.*, 104, pp. 585–593 (1987).

Dodd, Jane, and Thomas M. Jessell, "Cell Surface Glycoconjugates and Carbohydrate–Binding Proteins: Possible Recognition Signals in Sensory Neurone Development," *J. Exp. Biol.*, 124, pp. 225–238 (1986).

Durkin, Marian E., et al., "Amino Acid Sequence and Domain Structure of Entactin. Homology With Epidermal Growth Factor Precursor and Low Density Lipoprotein Receptor," *J. Cell Biol.*, 107, pp. 2749–2756 (1988).

Edgar David, et al., "The Heparin–Binding Domain of Laminin is Responsible for its Effects on Neurite Outgrowth and Neuronal Survival," *The EMBO Journal*, 3, pp. 1463–1468 (1984).

Edgar, David, "Neuronal Laminin Receptors," *TINS*, 12, pp. 248–251 (1989).

End, Peter, and Jurgen Engel, "Multidomain Proteins of the Extracellular Matrix and Cellular Growth," *Receptors for Extracellular Matrix* (McDonald, J. and Mecham. R., ed.), pp. 79–129 (1991).

FMC Corporation, "SeaPlaque® and SeaPrep® Agarose" (Product Information Literature), *FMC BioProducts Source Book*, FMC Corp., pp. 16, 26–30, 51, 54–106 (1988).

Friedlander, David R., et al., "Functional Mapping of Cytotactin Proteolytic Fragments Active in Cell–Substrate Adhesion," *J. Cell Biol.*, 107, pp. 2329–2340 (1988).

Fujiyama, C., et al., "Influence of Extracellular Matrix on the Proliferation and Differentiation of Adrenocortical Cells in Culture," *Path. Res. Pract.*, 189, pp. 1205–1214 (1993).

Gordon–Weeks, P.R., et al., "Transient Expression of Laminin Immunoreactivity in the Developing Rat Hippocampus," *J. of Neurocytology*, 18, pp. 451–463 (1989).

Grabham, Peter W., et al., "Vibronectin Is the Major Serum Protein Essential for NGF–Mediated Neurite Outgrowth from PC12 Cells," *Experimental Cell Research*, 202, pp. 337–344 (1992).

Graf, Jeanette, et al., "A Pentapeptide from the Lamin β1 Chain Mediates Cell Adhesion and Binds the 67 000 Laminin Receptor," *Biochemistry*, 26, pp. 6896–6900 (1987).

Graf, Jeannette, et al., "Identification of an Amino Acid Sequence in Laminin Mediating Cell Attachment, Chemotaxis, and Receptor Binding," *Cell*, 48, pp. 989–996 (1987).

Grant, Derrick S., et al., "Two Different Laminin Domains Mediate the Differentiation of Human Endothelial Cells into Capillary–like Structure In Vitro," *Cell*, 58, pp. 933–943 (1989).

Griess, Gary A., et al., "The Relationship of Agarose Gel Structure to the Sieving of Spheres During Agarose Gel Electrophoresis," *Biophysical Journal*, 65, pp. 138–148 (1993).

Guenard, Veronique, et al., "Syngeneic Schwann Cells Derived from Adult Nerves Seeded in Semipermeable Guidance Channels Enhance Peripheral Nerve Regeneration," *The Journal of Neuroscience*, 12, pp. 3310–3320 (1992).

Gumbiner, Barry M., "Proteins Associated with the Cytoplasmic Surface of Adhesion Molecules," *Neuron*, 11, pp. 551–564 (1993).

Hammarback, J.A., et al., "Guidance of Neurite Outgrowth by Pathways of Substratum–Absorbed Laminin," *J. of Neuroscience Research*, 13, pp. 213–220 (1985).

Hearn, Milton T.W., "1,1–Carbonyldiimidazole–Mediated Immobilization of Enzymes and Affinity Ligands," *Methods in Enzymology*, 135, pp. 102–117 (1987).

Hubbell, Jeffrey A., et al., "Surface–grafted Cell–binding Peptides in Tissue Engineering of the Vascular Graft," *Annals New York Academy of Sciences*, 665, pp. 253–258 (1992).

Ito, Yoshihiro, et al., "Materials for Enhancing Cell Adhesion by Immobilization of Cell–Adhesive Peptide," *Journal of Biomedical Materials Research,* 25, pp. 1325–1337 (1991).

Iwamoto, Yukihide, et al., "YIGSR, a Synthetic Lamin Pentapeptide, Inhibits Experimental Metastasis Formation," *Science,* 238, pp. 1132–1134 (1987).

Iwata, Mineo, and Carlson, Steven S., "A Large Chondroitin Sulfate Proteoglycan Has the Characteristics of a General Extracellular Matrix Component of Adult Brain," *The Journal of Neuroscience,* 13, pp. 195–207 (1993).

Jucker, M., "Fetal Rat Septal Cells Adhere to and Extend Processes on Basement Membrane, Laminin, and a Synthetic Peptide From the Laminin A Chain Sequence," *J. Neuroscience Research,* 28, pp. 507–517 (1991).

Kibbey, Maura C., et al., "β–Amyloid Precursor Protein Binds to the Neurite–Promoting IKVAV Site of Laminin," *Proc. Natl. Acad. Sci. USA,* 90, pp. 10150–10153 (1993).

Kleinman, Hynda K., et al., "The Role of Laminin in Basement Membranes and in the Growth, Adhesion, and Differentiation of Cells," *The Role of Extracellular Matrix in Development,* pp. 123–143 (1984).

Kleinman, Hynda K., et al., "Laminin in Neuronal Development," *Annals New York Acad. Sciences,* 580, pp. 302–310 (1990).

Kleinman, Hynda K., and Weeks, Benjamin S., "The Neural Cell Response to Laminin: Active Sites, Receptors, and Intracellular Signals," *Comments Developmental Neurobiology,* 1, pp. 251–266 (1991).

Koebe, Hans G., et al., "A New Approach to the Cryopreservation of Hepatocytes in a Sandwich Culture Configuration," *Cryobiology,* 27, pp. 576–584 (1990).

Krewson, Christine E., et al., "Cell Aggregation and Neurite Growth in Gels of Extracellular Matrix Molecules," *Biotechnology and Bioengineering,* 43, pp. 555–562 (1994).

Lawler, Jack, et al., "Cell Attachment to Thrombospondin: The Role of Arg–Gly–Asp. Calcium, and Integrin Receptors," *J. Cell Biol.,* 107, pp. 2351–2361 (1988).

Letourneau, Paul C., and Terri A. Shattuck, "Distribution and Possible Interactions of Actin–Associated Proteins and Cell Adhesion Molecules of Nerve Growth Cones," *Development,* 105, pp. 505–519 (1989).

Liesi, Paivi, "Do Neurons in the Vertebrate CNS Migrate On Laminin?" *The EMBO Journal,* 4, pp. 1163–1170 (1985).

Liesi, P. et al., "Neurons Cultured From Developing Rat Brain Attach and Spread Preferentially to Laminin," *J. Neuroscience Research,* 11, pp. 241–251 (1984).

Manthorpe, Marston, et al., "Laminin Promotes Neuritic Regeneration from Cultured Peripheral and Central Neurons," *J. Cell Biol.,* 97, pp. 1882–1890 (1983).

Massia, Stephen P., and Jeffrey A. Hubbell, "Covalent Surface Immobilization of Arg–Gly–Asp–and Try–Ile–Gly––Ser–Arg–Containing Peptides to Obtain Well–Defined Cell–Adhesive Substrates," *Analytical Biochemistry,* 187, pp. 292–301 (1990).

Mathis Georg A., et al., "Biochemical Characteristics of Hyperplastic Rat Bile Ductular Epithelial Cells Cultured 'On Top' and 'Inside' Different Extracellular Matrix Substitutes," *Cancer Research,* 48, pp. 6145–6153 (1988).

Matsuda, Takehisa, et al., "Development of a Novel Artificial Matrix with Cell Adhesion Peptides for Cell Culture and Artificial and Hybrid Organs," *Trans Am Soc Artif Intern Organs,* 35, pp. 677–679 (1989).

Matsushima, Hiroshi, and Emil Bogenmann, "Modulation of Neuroblastoma Cell Differentiation by the Extracellular Matrix," *Int. J. Cancer,* 51, pp. 727–732 (1992).

Matuoka, Koozi, et al., "Heparan Sulfate Enhances Growth of Transformed Human Cells," *Cell Structure and Function,* 9, pp. 357–367 (1984).

McCarthy, James B., et al., "Migration by Haptotaxis of a Schwann Cell Tumor Line to the Basement Membrane Glycoprotein Laminin," *J. Cell Biol.,* 97, pp. 772–777 (1983).

McCormack, M. L., et al., "Comparison of Dorsal and Ventral Spinal Root Regeneration Through Semipermeable Guidance Channels," *J. of Comparative Neurology,* 313, pp. 449–456 (1991).

McLoon, Steven C., et al., "Transient Expression of Laminin in the Optic Nerve of the Developing Rat," *J. of Neuroscience,* 8, pp. 1981–1990 (1988).

Murata, Jun, et al., "Inhibitory Effect of a Synthetic Polypeptide, poly (Tyr–Ile–Gly–Ser–Arg), On the Metastatic Formation of Malignant Tumor Cells," *Int. J. Biol. Macromol.,* 11, pp. 97–99, (1989).

Nieke, Joachim, and Melitta Schachner, "Expression of the Neural Cell Adhesion Molecules L1 and N–CAM and Their Common Carbohydrate Epitope L2/HNK–1 During Development and After Transection of the Mouse Sciatic Nerve," *Differentiation,* 30, pp. 141–151 (1985).

Perris, Roberto, and Marianne Bronner–Fraser, "Recent Advances in Defining the Role of the Extracellular Matrix in Neural Crest Development," *Comments Dev. Neurobiology,* 1, pp. 61–83 (1989).

Peyronnard, Jean–Marie, and Louise Charron, "Motor and Sensory Neurons of the Rat Sural Nerve: A Horseradish Peroxidase Study," *Muscle & Nerve,* 5, pp. 654–660 (1982).

Pierschbacher, Michael D., and Erkki Ruoslatiti, "Cell Attachment Activity of Fibronectin Can Be Duplicated By Small Synthetic Fragments of the Molecule," *Nature,* 309, pp. 30–33 (1984).

Pixley, S.K.R., and C.W. Cotman, "Laminin Supports Short––Term Survival of Rat Septal Neuron in Low–Density, Serum–Free Cultures," *J. Neuroscience Research,* 15, pp. 1–17 (1986).

Ray, Jasohara, et al., "Proliferation, differentiation, and long–term culture of primary hippocampal neurons," *Proc. Natl. Acad. Sci. USA,* 90, pp. 3602–3606 (1993).

Refojo, Miguel F., "Permeation of Water Through Some Hyrogels," *J. Applied Polymer Science,* 9, pp. 3417–3426 (1965).

Richards, L.J., " *De novo* generation of neuronal cells from the adult mouse brain," *Proc. Natl. Acad. Sci. USA,* 89, pp. 8591–8595 (1992).

Rogers, Sherry L., et al., "Distribution of Laminin in the Developing Peripheral Nervous System of the Chick," *Developmental Biology,* 113, pp. 429–435 (1986).

Ruoslahti, Erkki, and Michael D. Pierschbacher, "New Perspectives in Cell Adhesion: RGD and Integrins," *Science,* 238, pp. 491–497 (1987).

Ruoslahti, Ekki, and John C. Reed, "Anchorage Dependence, Integrins, and Apoptosis," *Cell,* 77, pp. 477–478 (1994).

Saiki, I., et al., "Antimetastatic Effects of Synthetic Polypeptides Containing Repeated Structures of the Cell Adhesive Arg–Gly–Asp (RGD) and Tyr–Ile–Gly–Ser–Arg (YIGSR) Sequences," *Br. J. Cancer,* 60, pp. 722–728 (1989).

Sanes, Joshua R., "Extracellular Matrix Molecules That Influence Neural Development," *Ann. Rev. Neurosci.,* 12, pp. 491–516 (1989).

Sephel, G.C., et al., "Laminin a Chain Synthetic Peptide Which Supports Neurite Outgrowth," *Biochemical and Biophysical Research Communications,* 162, pp. 821–829 (1989).

Smalheiser, Neil R., et al., "Laminin As Substrate for Retinal Axons In Vitro," *Dev. Brain Research,* 12, pp. 136–140 (1984).

Steele, J. G., and B. A. Dalton, "Neurite–Promoting Activity From Fetal Skeletal Muscle: Immunological Comparison With Laminin," *J. Neuroscience Research,* 17, pp. 119–127 (1987).

Suzuki, Shintaro, et al., "Complete Amino Acid Sequence of Human Vitronectin Deduced from cDNA. Similarity of Cell Attachment Sites in Vitronectin and Fibronectin," *The EMBO Journal,* 4, pp. 2519–2524 (1985).

Tashiro, Ken–ichiro, et al., "A Synthetic Peptide Containing the IKVAV Sequence from the A Chain of Laminin Mediates Cell Attachment, Migration, and Neurite Outgrowth," *The Journal of Biological Chemistry,* 264, pp. 16174–16182 (1989).

Telios Pharmaceuticals, "Integrins: An Update on the Rapid Growth of Research Topics," in *ECM Connections,* a publication of Telios Pharmaceuticals, San Diego, CA (Jun. 1992).

Telios Pharmaceuticals, "Pep Tite–2000" (Product Information Memorandum), Telios Pharmaceuticals, San Diego, CA.

Tomaselli, K.J., et al., "A Neuronal Cell Line (PC12) Expresses Two $\beta_1$–Class Integrins—$\alpha_1\beta_1$ and $\alpha_3\beta_1$—That Recognize Different Neurite Outgrowth–Promoting Domains in Laminin," *Neuron,* 5, pp. 651–662 (1990).

Valentini, R.F., et al., "Collagen– and Laminin–Containing Gels Impede Peripheral Nerve Regeneration through Semipermeable Nerve Guidance Channels," *Experimental Neurology,* 98, pp. 350–356 (1987).

Wehrle, Bernhard, and Matthias Chiquet, "Tenascin is Accumulated Along Developing Peripheral Nerves and Allows Neurite Outgrowth In Vitro," *Development,* 110, pp. 401–405 (1990).

Woerly, S., et al., "Synthetic Polymer Matrices for Neural Cell Transplantation," *Cell Transplantation,* 2, pp. 229–239 (1993).

Zhou, Feng C., "Four Patterns of Laminin–Immunoreactive Structure in Developing Rat Brain," *Developmental Brain Research,* 55, pp. 191–201 (1990).

FIG. 2
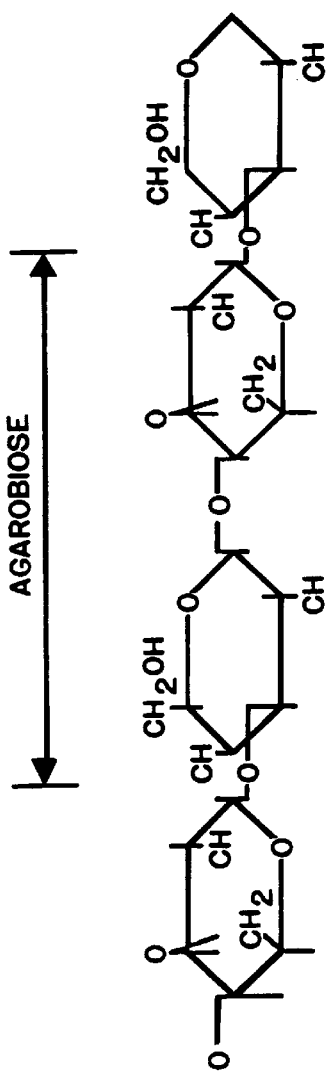
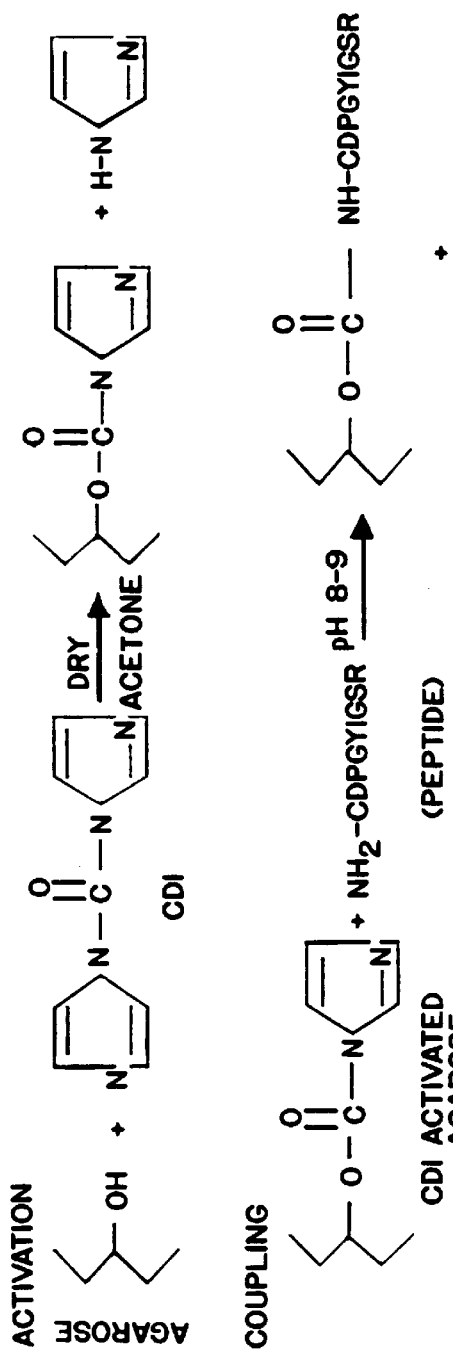

NERVE GUIDANCE CHANNEL CONTAINING BIOARTIFICIAL THREE-DIMENSIONAL HYDROGEL EXTRACELLULAR MATRIX DERIVATIZED WITH CELL ADHESIVE PEPTIDE FRAGMENT

FIELD OF THE INVENTION

This invention relates to compositions and methods for a bioartificial extracellular matrix.

BACKGROUND OF THE INVENTION

Tissue engineering in the nervous system deals with the functional replacement of damaged tissues and nervous system regeneration.

The ability to organize cells in three dimensions (3-D) is an important component of tissue engineering. The behavior of cells is influenced both by their intrinsic genetic programs and their extracellular environment. The extracellular environment includes 'passive' structural components and biologically 'active' components.

Most cells in multicellular organisms are in contact with an intricate meshwork of interacting, extracellular macromolecules that constitute the extracellular matrix (ECM). These macromolecules, mainly proteins and polysaccharides, are secreted locally and assemble into an organized 3-D meshwork in the extracellular spaces of most tissues. ECM molecules include glycosaminoglycans, and proteoglycans such as chrondroitin sulfate, fibronectln, heparin sulfate, hyaluron, dermatan sulfate, keratin sulfate, laminin, collagen, heparan sulfate proteoglycan, and elastin. In addition to serving as a universal biological glue, ECM molecules also form highly specialized structures such as cartilage, tendons, basal laminae, and (in conjunction with secondary deposition of calcium phosphate) bone and teeth. Alberts et al., *Molecular Biology of the Cell*, Garland, NY, pp. 802–24 (1989).

Extracellular matrices modulate the organization of the intracellular cytoskeleton, cell differentiation and the spatial architecture of cells and tissues. In fact, the ECM plays a critical role in regulating the behaviour of cells that contact it by influencing cellular development, migration, proliferation, differentiation, shape, polarity and metabolic function.

Several peptide active sites responsible for cell attachment have been identified in various ECM molecules.

In vivo, laminin (LN) immunoreactivity has been detected in several regions of the embryo including muscles (Chui and Sanes, *Dev. Biol.*, 103, pp. 456–67 (1984)), spinal cord (Azzi et al., *Matrix*, 9, pp. 479–85 (1989), spinal roots (Rogers et al., *Dev. Biol.*, 113, pp. 429–35 (1986)), optic nerve (McLoon et al., *J. Neurosci.*, 8, pp. 1981–90 (1988)), cerebral cortex (Liesi, *EMBO*, 4, pp. 1163–70 (1985); Zhou, *Dev. Brain Res.*, 55, pp. 191–201 (1990)), hippocampus (Gordon-Weeks et al.,*J. Neurocytol.*, 18, pp. 451–63 (1989)) and the medial longitudinal fasciculus of the midbrain (Letourneau et al., *Development*, 105, pp. 505–19 (1989)).

The tripeptidic sequence RGD (ArgGlyAsp; $AA_2$–$AA_4$ of SEQ ID NO:2) has been identified to be responsible for some of the cell adhesion properties of fibronectin (Pierschbacher and Ruoslahti, *Science*, 309, pp. 30–33 (1984)), laminin (Grant et al., *Cell*, 58, pp. 933–43 (1989)), entactin (Durkin et al., *J. Cell. Biol.*, 107, pp. 2329–40 (1988)), vitronectin (Suzuki et al., *EMBO*, 4, pp. 2519–24 (1985)), collagen I (Dedhar et al., *J. Cell. Biol.*, 107, pp. 2749–56 (1987)), collagen IV (Aumailley et al., *Exp. Cell Res.*, 187, pp. 463–74 (1989)), thrombospondin (Lawler et al., *J. Cell. Biol.*, 107, pp. 2351–61 (1988)) and tenascin (Friedlander et al., *J. Cell. Biol.*, 107, pp. 2329–40 (1988)).

The sequence YIGSR (TyrIleGlySerArg; $AA_5$–$AA_9$ of SEQ ID NO:1), found on the B1 chain of laminin, promotes epithelial cell attachment (Graf et al., *Biochemistry*, 26, pp. 6896–900 (1987)) and inhibits tumor metastasis (Iwamoto et al., *Science*, 238, pp. 1132–34 (1987)).

The IKVAV sequence found on the A chain of laminin, has been reported to promote neurite outgrowth (Tashiro et al., *J. Biol. Chem.*, 264, pp. 16174–182 (1989); Jucker et al.,*J. Neurosci. Res.* 28, pp. 507–17 (1991)).

All of the studies using these peptidic sequences of cell attachment and neurite promotion were conducted on flat two-dimension substrates (Smallheiser et al., *Dev. Brain Res.*, 12, pp. 136–40 (1984); Graf et al., *Biochemistry*, 26, pp. 6896–900 (1987); Sephel et al., *Biochem. Biophys. Res. Comm.*, 2, pp. 821–29 (1989); Jucker et al., *J. Neurosci. Res.*, 28, pp. 507–17 (1991)). The physical and chemical nature of the culture substrate influences cell attachment and neurite extension. The physical microstructure of a 2-D culture substrate can influence cell behavior. The use of permissive and non-permissive culture surface chemistries facilitates nerve guidance in 2-D. The cell attachment regulating function of various serum proteins like albumin and fibronectin is dependent on the chemistries of the culture substrates that they are adsorbed onto.

Gene expression is reported to be regulated differently by a flat 2-D substrate as opposed to a hydrated 3-D substrate. For example, monolayer culture of primary rabbit articular chondrocyte and human epiphyseal chondrocyte on 2-D tissue culture substrates causes primary chondrocyte to lose their differentiated phenotype. The differentiated chondrocyte phenotype is re-expressed when they are cultured in 3-D agarose gels (Benya and Shaffer, *Cell*, 30, pp. 215–24 (1982); Aulthouse, et al., *In Vitro Cell Dev. Bio.*, 25, pp. 659–68 (1989)).

Similarly, alkaline phosphatase gene expression in primary bile ductular epithelial cells is differentially regulated when they are cultured in 3-D Matrigel®, collagen I or agarose gels as opposed to 2-D cultures (Mathis et al., *Cancer Res.*, 48, pp. 6145–53 (1988)).

Therefore, 3-D presentation of ECM components may better mimic the in vivo environment in influencing cell or tissue response. In particular, in vivo use of ECM biomolecules may require such a 3-D system for optimal efficacy. The development of a defined, bioartificial 3-D matrix that presents ECM molecules, or active portions thereof, would facilitate tissue engineering in the nervous system by allowing in vitro and in vivo cell manipulation and cell culture in 3-D. See, e.g., Koebe et al., *Cryobiology*, 27, pp. 576–84 (1990).

In addition, there is a need to develop a defined, biosynthetic matrix, because the tumorogenic origins of some commercially available ECM, e.g., Matrigel® mouse sarcoma derived ECM, render it unattractive for some in vitro and in viva applications. Further, naturally occuring ECM components such as collagen may be enzymatically degraded in the body while a synthetic ECM is less likely to be degraded.

SUMMARY OF THE INVENTION

This invention provides a three-dimensional hydrogel based, biosynthetic, extracellular matrix (ECM) equivalent, and method of making same. Agarose matrices having a chemistry amenable to derivatization with various ECM adhesive peptides and proteins, are preferred in forming the 3-D hydrogel substrates of this invention. These biologically active 3-D templates may be useful in facilitating tissue regeneration or replacement.

BRIEF DESCRIPTION OF THE DRAWINGS

FIG. 2. Schematic of an agarobiose unit and the carbonyldiimidazole coupling chemistry for the immobilization of CDPGYIGSR (CysAspProGlyTyrIleGly SerArg; SEQ ID NO:1) oligopeptide to agarose gels.

DETAILED DESCRIPTION OF THE INVENTION

Figure 1:
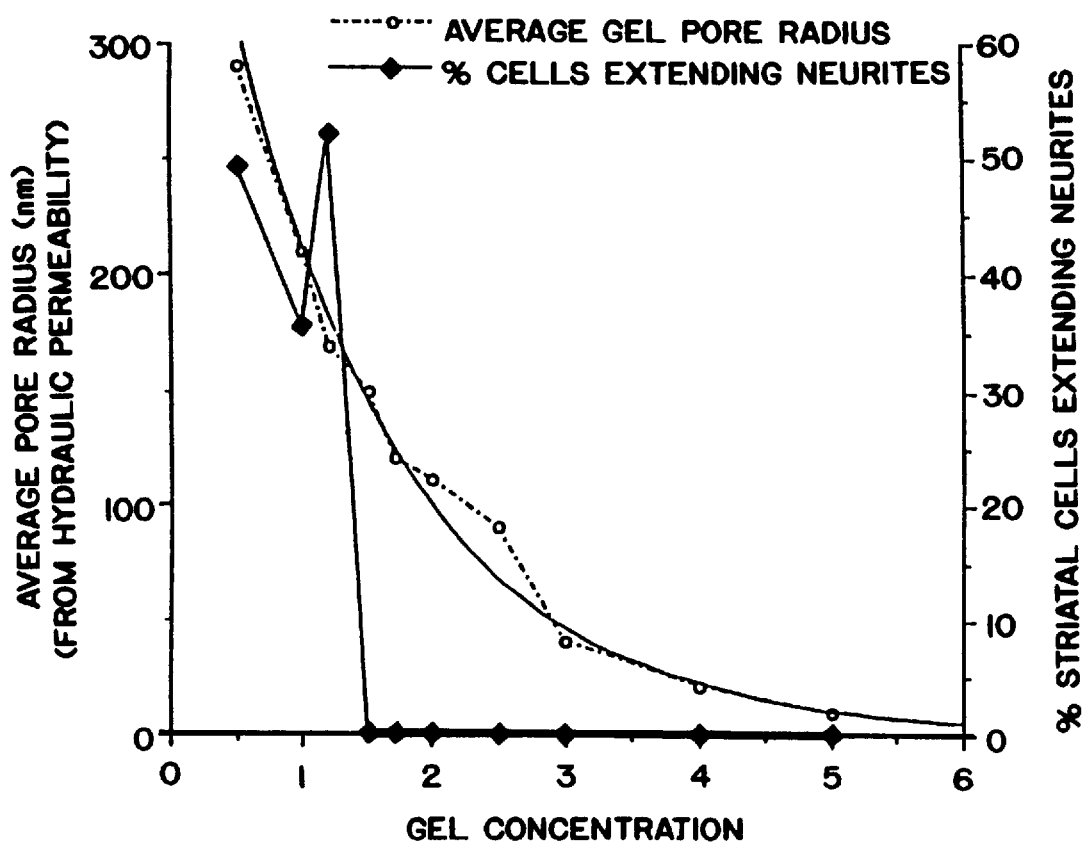
FIG. 1. A double Y-axis plot depicting the influence of agarose gel concentration on average pore radius (Y1) and percent striatal cells extending neurites (Y2) after 72 hours in culture. Pore radius was calculated by hydraulic permeability measurements of the different gel concentrations. Solid line through pore radii data points is an exponential fit with $r^2=0.985$.

This invention provides a biosynthetic, hydrogel-based, three-dimensional bioartificial ECM. The bioartificial extracellular matrices of this invention offer the possibility of manipulating cells in 3-D, and may be used as three dimensional templates for tissue engineering efforts in vitro and in vivo.

The term "nerve" means both nonfascicular and polyfascicular nerves.

The term "active factor" or "growth factor" includes any active analogs, active fragments, or active derivatives thereof.

Any suitable hydrogel may be used as the substrate for the bioartificial extracellular matrices of this invention. Compositions that form hydrogels fall into three classes. The first class carries a net negative charge (e.g., alginate). The second class carries a net positive charge (e.g., collagen and laminin). Examples of commercially available extracellular matrix component hydrogels include Matrigel™ and Vitrogen™. The third class is net neutral in charge (e.g., highly crosslinked polyethylene oxide, or polyvinylalcohol).

A hydrogel suitable for use in this invention is preferably a defined polymer, most preferably a polymer that is synthetic or can be prepared from a naturally occurring, non-tumorigenic source, free of undesired biological (e.g., bacterial or viral), chemical or other contaminants. Most preferred as the matrix substrate are well characterized hydrogels that permit presentation of only the desired ECM adhesion molecule or adhesive peptide fragement in 3-D, substantially free of undesired adhesion motifs.

Matrigel™ is not a defined substrate and also less desirable since it is derived from a murine sarcoma line. In addition, not all synthetic polymer hydrogels are suitable. For example, the use of acrylic based hydrogels by Woerly et al., Cell Transplantation, 2, pp. 229–39 (1993) presents the possibility of cytotoxicity because entrapment of neuronal cells is done concomitantly with the cross-linking reaction in the presence of free radical initiators.

Polymers that may be useful as hydrogel matrix substrate materials include high molecular weight polyethylene oxide (PEO) and hyaluronate. Stabilized hyaluronate is commercially available (Fidia Advanced Biopolymers). Various PEO polymers are also commercially available.

Polysaccharides are a class of macromolecules of the general formula $(CH_2O)_n$ which are useful as the hydrogel substrate in the present invention. Polysaccharides include several naturally occuring compounds, e.g., agarose, alginate and chitosan. We prefer agarose.

Agarose is a clear, thermoreversible hydrogel made of polysaccharides, mainly the alternating copolymers of 1,4 linked and 3,6-anhydro-α-L-galactose and 1,3 linked β-D-galactose. Two commercially available agaroses are Sea-Prep® and SeaPlaque® agarose (FMC Corp. Rockland, Me.). SeaPrep® is a hydroxyethylated agarose that gels at 17° C. The particular suitability of a hydrogel as a biomaterial stems from the similarity of its physical properties to those of living tissues. This resemblance is based on its high water content, soft rubbery consistency and low interfacial tension. The thermoreversible properties of agarose gels make it possible for agarose to be a liquid at room temperature allowing for easy mixing of cell-gel solution and then cooling to 4° C. causes gelation and entrapment of cells. This is a comparatively benign process, free of chemicals toxic to the cells.

We prefer an agarose concentration of 0.50 to 1.25% (w/v), most preferably 1.0%, for the permissive layers of the hydrogel matrix.

Several physical properties of the hydrogel matrices of this invention are dependent upon gel concentration. Increase in gel concentration may change the gel pore radius, morphology, or its permeability to different molecular weight proteins.

Gel pore radius determination can be determined by any suitable method, including hydraulic permeability determination using a graduated water column, transmission electron microscopy and sieving spheres of known radius through different agar gel concentrations. See, e.g., Griess et al., *Biophysical J.*, 65, pp. 138–48 (1993). We prefer hydraulic permeability-based pore radius determination, as the method most sensitive to changes in gel concentration.

Measurement of gel hydraulic permeability using a graduated water column enabled the calculation of average pore radius for each of the gel concentrations studied. The average gel pore radius fell exponentially as the gel concentration increased. The slope of the curve indicated the sensitivity of pore radius to gel concentration. The average gel pore radius preferably varies between 120–290 nm, and is most preferably approximately 150 nm. The pore radius of the 1.25% threshold agarose gel concentration was 150 nm.

The agarose hydrogels of this invention may be used as a carrier to present various ECM proteins or peptides, e.g., laminin fibronectin, and/or their peptidic analogs in 3-D. The chemistry of agarose permits easy modification with such ECM adhesive proteins and/or peptides. We prefer covalent immobilization of ECM proteins to the hydrogel backbone. Such immobilization is important because the physical blending of low molecular weight oligopeptides with hydrogels will not retain the peptides in the gel. Further, covalent immobilization prevents the possible saturation of cell surface receptors by 'free-floating' ECM molecules in hydrogel-ECM molecule blends.

Any suitable coupling system may be used for derivatization. Most preferably, covalent coupling using a bi-functional imidazole coupling agent, e.g., 1'1 carbonyldiimidazole, is used. This coupling chemistry does not alter the physical structure of the gel significantly.

The bioartificial hydrogel extracellular matrices of this invention are useful for presenting in 3-D full length extracellular matrix proteins involved in cell adhesion. In addition, peptide fragments of such adhesion molecules that contain cell binding sequences may also be used (i.e., adhesive peptide fragments). Several such adhesive peptide fragments are known in the art. A particular peptide fragment can be tested for its binding ability or adhesive capacity according to standard techniques.

The bioartificial hydrogel matrices of this invention can be used to present ECM adhesion molecules, or adhesive peptide fragments thereof, in 3-D to a variety of cell types. These cell types include any cell that is normally in contact with the ECM in vivo, or any cell bearing a cell surface receptor capable of binding to an ECM adhesion molecule or adhesive peptide fragment thereof.

Useful cells include epithelial cells, endothelial cells, fibroblasts, myoblasts, chondroblasts, osteoblasts, and neural stem cells (Richards et al., *PNAS* 89, pp. 8591–95 (1992); Ray et al., *PNAS* 90, pp. 3602–06 (1993)). Other cells that may be useful in the methods and compositions of this invention include, Schwann cells (WO 92/03536), astrocytes, oligodendrocytes and their precursors, adrenal chromaffin cells, and the like.

Stem cells represent a class of cells which may readily be expanded in culture, and whose progeny may be terminally differentiated by the administration of a specific growth factor. See, e.g., Weiss et al. (PCT/CA 92/00283).

Myoblasts are muscle precursor cells originally derived from mesodermal stem cell populations, e.g., L-6 and β-CH3 cells. Primary myoblasts can be readily isolated from tissue taken from an autopsy or a biopsy, and can be purified and expanded. Myoblasts proliferate and fuse together to form differentiated, multi-nucleated myotubes. Myotubes no longer divide, but continue to produce muscle proteins. While proliferating, myoblasts may readily be genetically engineered to produce therapeutic molecules. Myoblasts are capable of migrating and fusing into pre-existing fibers.

It will be appreciated that the choice of ECM adhesion molecule or adhesive peptide fragment for use in the bioartificial ECM matrix will depend upon the desired target cell type. See, e.g., Kleinman, U.S. Pat. No. 4,829,000; End and Engel, "Multidomain Proteins Of The Extracellular Matrix And Cellular Growth", in McDonald and Mecham *Biology of Extracellular Matrix Series*, Academic Press, N.Y., pp. 79–129 (1991). One of skill in the art can routinely assay any particular ECM molecule or adhesive peptide fragment motif for its adhesive capacity for a chosen cell type.

Thus, according to the compositions and methods of this invention, it may be possible to influence the behavior (i.e., development, migration, proliferation, differentiation, shape, polarity, and/or metabolic function) of any ECM-responsive cell type, by providing the appropriate ECM-mediated molecular cues.

In some embodiments, the hydrogel ECM matrix can be derivatized with the appropriate ECM adhesion molecules or adhesive peptide fragments and implanted into a desired location in a host, e.g., a mammal, preferably a human. In these embodiments, the matrix acts as a support for tissue regeneration, whereby the host cells infiltrate the matrix. In the presence of the appropriate 3-D molecular cues in the matrix host tissue regeneration is facilitated.

Such embodiments have use, for example, in cartilage or tendon regeneration by derivatizing the matrix with ECM adhesion molecules or adhesive peptide fragments that favor chondrocyte invasion. Similarly, the matrices of this invention may be useful in promoting muscle, bone or skin regeneration by presenting the appropriate molecular cues to influence myoblast, osteoblast or epithelial cell behavior. In a preferred embodiment, the bioartificial matrices of this invention are used to promote nerve regeneration, in nerve guidance channels.

In other embodiments, the bioartificial matrices of this invention can be pre-seeded with cells, whereby the cells are suspended in the matrix and exposed to the appropriate molecular cues in 3-D. These cell-seeded matrices are useful in tissue replacement protocols. According to these embodiments, tissue can be reconstituted in vitro and then implanted into a host in need thereof. For example, cardiac myoblasts may be suspended in the derivatized hydrogel matrices of this invention to create a tissue patch of a thickness corresponding to the cardiac wall. The reconstituted cardiac patch could then be implanted, as part of a tissue replacement therapy.

Similar protocols for cartilage, tendon, bone, skin, nerve, blood vessels and other tissues are contemplated. The ability to cast hydrogels, e.g., agarose, into a variety of shapes, as well the ability to fabricate "permissive" gel concentrations enables the production of bioartificial matrices that can influence cell behavior in defined planes or through defined "tracts".

It will be appreciated that according to the foregoing embodiments, the cells may be xenografts, allografts or autografts, preferably allografts, most preferably, autografts. Surgical procedures for implanting such cells are known. See, e.g., Gage, U.S. Pat. No. 5,082,670.

In other embodiments it may be desirable to encapsulate the cell-seeded matrix in a semi-permeable membrane to form a bioartificial organ. Such bioartificial organs are well known in the art. See, e.g., WO 92/019195, incorporated herein by reference. In these embodiments the metabolic function of the encapsulated cells may be controlled by the ECM adhesion molecule or adhesive peptide fragment presented in 3-D. The encapsulated cells can be influenced to produce a biologically active molecule that may function within the encapsulated cells, or be released or secreted from the encapsulated cells, to exert a therapeutic effect on the host. This allows precise control over cell behaviour at a fixed location in the host body.

In a preferred embodiment, laminin-derived oligopeptidic fragments, an RGD-containing sequence (ArgGlyAsp; $AA_2$–$AA_4$ of SEQ ID NO:2), a YIGSR-containing sequence (TyrIleGlySerArg; $AA_5$–$AA_9$ of SEQ ID NO:1) and/or an IKVAV-containing sequence (IleLysValAlaVal; $AA_{11}$–$AA_{15}$ of SEQ ID NO:3), are coupled to the hydroxyl backbone of agarose, using any suitable method. Most preferably, the oligopeptidic fragments GRGDSP (GlyArgGlyAspSerPro; SEQ ID NO:2), CDPGYIGSR (CysAspProGlyTyrIleGlySerArg; SEQ ID NO:1), or the 19-mer water-soluble amino acid sequence C S R A R K Q A A S I K V A V S A D R (CysSerArgAlaArgLysGlnAlaAlaSer IleLysValAla-ValSerAlaAspArg; SEQ ID NO:3) are used.

CDPGYIGSR (CysAspProGlyTyrIleGlySerArg; SEQ ID NO:1) has been shown to evoke only 30% of the maximal response obtained by laminin in chemotactic functions with melanoma cells (Graf et al., *Biochemistry*, 26, pp. 6896–900 (1987)). Thus, the use of full length ECM molecules may elicit more significant cellular effects. However, the use of minimal oligopeptides creates a more stringent substrate condition and facilitates the testing of the gel system without the potent biological effects of full length proteins eclipsing the gel's physical effects. This enables the development and testing of a system with a base physical structure to support cell viability and influence cell behaviour. The hydrogel matrix can then be rendered progressively more permissive by the use of appropriate covalently-coupled cell adhesion or extracellular matrix molecules.

The 3-D matrices of this invention may be further modified, preferably chemically modified, to include hexosamine residues. Carbohydrates may be involved in cell adhesion. Dodd and Jessel, *J. Exp. Biol.*, 124, 00. 225–38 (1986).

In another preferred embodiment, the compositions of this invention may be used in neural cell transplantation. The ability of biosynthetic hydrogels to organize, support and direct neurite extension from neural cells may also be useful for applications such as 3-D neural cell culture and nerve regeneration. The bioartificial extracellular matrices of this invention may potentially carry one or more of the several cell adhesion molecules that have been identified to play an important role in cell migration and neurite extension in the developing nervous system, including N-CAM and Ng-CAM (Crossin et al., *Proc. Natl. Acad. Sci.*, 82, pp. 6942–46 (1985); Daniloff et al., *J. Neurosci.*, 6, pp. 739–58 (1986)), tenascin (Wehrle et al., *Development*, 1990, pp. 401–15 (1990)) and L1 (Nieke and Schachner, *Differentiation*, 30, pp. 141–51 (1985)). Among extracellular matrix glycoproteins, laminin has been shown to be one of the most potent inducers of neurite outgrowth in vitro. It is a component of the Schwann cell basal lamina and is thought to be involved in axonal regeneration in vivo (Baron-Van-Evercooren et al., *J. Neurosci. Res.*, 8, pp. 179–93 (1983); Manthorpe et al., *J. Cell. Biol.*, 97, pp. 1882–90 (1983); Rogers et al., *Dev. Biol.*, 113, pp. 429–35 (1983).

LN has also been found to enhance attachment of many neural cell types (McCarthy et al., *J. Cell. Biol.*, 97, pp. 772–77 (1983); Liesi et al., *J. Neurosci. Res.*, 11, pp. 241–51 (1984); Hammarback et al., *J. Neurosci. Res.*, 13, pp. 213–20 (1985); Kleinman et al., *Annals NY Acad. Sci.*, 580, pp. 302–10 (1990), increase the survival of sympathetic and septal neurons (Edgar et al., *EMBO*, 3, pp. 1463–68 (1984); Pixley et al., *J. Neurosci. Res.*, 15, pp. 1–17 (1986), and stimulate neurite outgrowth in many peripheral and central neurons (Baron Van Evercooren et al., *J. Neurosci. Res.*, 8, pp. 179–93 (1983); Manthorpe et al., *J. Cell. Biol.*, 97, pp. 1882–90 (1983); Rogers et al., *Dev. Biol.*, 113, pp. 429–35 (1983); Steele et al., *J. Neurosci. Res.*, 17, pp. 119–27 (1987).

LN and other ECM constituents influence neuronal development in both the peripheral and the central nervous systems. Hence, presenting ECM-oligopeptide derivatized agarose gels to the regenerating environment in 3-D may enhance nerve regeneration when introduced in appropriate animal models.

The complex glycoprotein and proteoglycan components of the extracellular matrix are thought to provide permissive pathways for neural cell migration and neurite extension during development. Cell-cell and cell-extracellular matrix (ECM) interactions appear to regulate various aspects of neuronal cell differentiation including neural cell migration and neurite extension. Sanes, *Ann. Rev. Neurosci.*, 12, pp. 491–516 (1989).

Anatomical studies of neural development show that the migratory pathways of pioneer neurons seem to consist of a 3-D ECM that is organized into a network of fibrils and granules. The chemotropic attraction of neuronal growth cones from their target areas, coupled with a permissive three dimensional maze comprised of ECM molecules like laminin (LN) and fibronectin (FN) and some cell free spaces filled with highly hydrates hyaluronic acid, is thought to play an important role in the development of embryonic nervous system.

Laminin (LN), an ECM molecule derived from basal lamina, promotes neurite outgrowth in a wide variety of neural cells including dorsal root ganglia (DRGs) and PC12 cells, a cell line derived from a rat pheochromocytoma. Kleinman et al., *Annals NY Acad. Sci.* 580, pp. 302–10 (1990).

In development, the pathways followed by neural crest cells and the growth cones of pioneer neural cells contain several ECM constituents, including fibronectin, laminin, tenascin, thrombospondin and hyaluronic acid. Perris and Bronner-Fraser, *Comments Dev. Neurobiol.*, 1, pp. 61–83 (1989).

Thus, in one embodiment the agarose matrix is derivatized with neurite promoting agents and growth factors to specifically enhance neurite extension in agarose gels. It has been shown that the activity of the neurite promoting protein laminin is enhanced after it is complexed with heparin sulfate proteoglycan which helps organize specific molecular interactions more favorable for neuritic outgrowth.

Integration of transplanted cells into host tissue results from growth of transplanted neurons, and from regeneration of axons from host neurons damaged during the transplantation, with the establishment of a functional interface, including graft-host interconnections and synaptic relationships. Woerly et al., *Cell Transplantation*, 2, pp. 229–39 (1993). The 3-D agarose matrices of this invention may serve as a support for directed growth of axons. We prefer neural stem cells isolated according to Weiss et al., PCT/CA92/00283, most preferably human stem cells.

The physio-chemical environment of various cells and tissues in vitro may be tailored to evoke particular and specific responses from them. Specific ECM peptides may be important in determining the degree of facilitation or permissivity to neurite outgrowth from neural cells. In particular, the nature of the peptide presented in 3-D can influence neurite extension. Further, cell types may be differently affected by a chosen peptide.

Neurite extension from PC12 cells in two-dimensions is enhanced by the IKVAV (IleLysValAlaVal; $AA_{11}$–$AA_{15}$ of SEQ ID NO:3) fragment of LN (Tashiro et al., *J. Biol. Chem.*, 264, pp. 16174–182 (1989)). PC12 cells possess a 110 kDa cell surface receptor (Kibbey et al., *Proc. Natl. Acad. Sci.*, 90, pp. 10150–53 (1993)) which has been postulated to be the binding site for the IKVAV (IleLysValAlaVal; $AA_{11}$–$AA_5$ of SEQ ID NO:3) sequence.

In a specific embodiment, agarose gels are derivatized with an IKVAV-containing sequence (IleLysValAlaVal; $AA_{11}$–$AA_{15}$ of SEQ ID NO:3) to promote neurite extension in PC12 cells.

The presence of nerve growth factor (NGF) may be required for neurite extension. See, e.g., Sephel et al., *Biochem. Biophys. Res. Comm.*, 2, pp. 821–29 (1989). These growth factors may be incorporated into the channel membrane (U.S. Pat. No. 5,011,486), or may be continuously provided within the channel by seeding the channel with cells that secrete the desired molecules, or a slowly released polymeric insert. See, e.g, U.S. Pat. Nos. 5,156,844 and 5,106,627. Such methods overcome problems associated with short half lives of various of the growth factors, and problems with non-continuous or uncontrolled delivery of these factors.

In another specific embodiment, agarose derivatized with an RGD-containing sequence (ArgGlyAsp; $AA_2$–$AA_4$ of SEQ ID NO:2), an CDPGYIGSR-containing sequence (CysAspProGlyTyrIleGlySerArg; SEQ ID NO:1), IKVAV-containing sequence (IleLysValAlaVal; $AA_{11}$–$AA_{15}$ of SEQ ID NO:3) or a cocktail (PEPMIX) containing a mixture of all three sequences, was used to promote neurite extension in E9 chick dorsal root ganglia.

In another method of this invention, lamination of alternating non-permissive, permissive and non-permissive gel layers permits the creation of 3-D cell growth or migration "tracts" in vitro. The agarose concentration for the non-permissive layer can be an agarose concentration greater than 1.25%, preferably 2.0% or greater.

In one embodiment, lamination of gel concentrations 2%:1%:2%, with the 1% gel layer carrying neural cells, e.g., dorsal root ganglia, can facilitate the creation of 3-D neural 'tracts'. Fabrication of the directed 3-D neural tracts of this invention can be achieved by physically casting neurite-extension permissive and non-permissive gels in a controlled manner. Such casting methods are known in the art.

The factors controlling nerve regeneration across a gap following transection injury are not fully understood. Regeneration of severed nerves does not normally include proliferation of nerve cells. However, the injured nerve cell will extend neurites that growth distally and attempt to reenter the intact neurilemmal sheath of the distal portion of the severed nerve. Conventional techniques for repair involve aligning the severed ends of the fascicles. This manipulation and suturing stimulates growth and/or migration of fibroblasts and other scar-forming, connective tissue cells. The scar tissue prevents the regenerating axons in the proximal stump from reaching the distal stump to reestablish a nerve charge pathway.

Various nerve guidance channels have been developed in attempts to overcome these problems. See, e.g. U.S. Pat. Nos. 5,030,225 and 5,092,871. One critical event in regeneration across a gap in smooth-walled silicone elastomer tubes is the formation of a fibrin cable bridge which serves as a scaffold for migrating cells and elongating axons. Schwann cells, axons, endothelial cells and fibroblasts subsequently enter the gap region and orient into regeneration units, blood vessels and epineurial and perineurial tissue, respectively. Aebisher et al., *Brian Research*, 531, pp. 211–18 (1990).

The agarose hydrogel compositions of this invention may be useful in nerve guidance channels. Such nerve guidance channels are well known in the art. Synthetic guidance channels have been used as inert conduits providing axonal guidance, maintaining growth factors, and preventing scar tissue invasion. Permselective channels with a molecular weight cut-off of 50,000 daltons allowed regeneration of nerves in a mouse sciatic nerve model. The regenerated nerves were characterized by fine epineurium and high numbers of myelinated axons. Aebischer et al., "The Use Of A Semi-Permeable Tube As A Guidance Channel For A Transected Rabbit Optic Nerve", In Gash & Sladek [Eds] *Progress in Brain Research*, 78, pp. 599–603 (1988).

Permselective channels may support regeneration by allowing inward passage of nutrients and growth or trophic factors from the external host environment, while preventing the inward migration of scar-forming cells. Cells participating in the wound healing phenomena are known to release various peptide growth factors. Several of these factors have molecular weights in the range 10–40,000 daltons. For example, activated macrophages secrete numerous growth factors, including NGF, bFGF, and apolipoprotein E.

Schwann cells distal to the nerve injury express low affinity NGF receptors, as well as apolipoprotein B and E receptors. Binding of apolipoprotein E to these receptors may enhance lipid uptake which can eventually be used in remyelination. Aebischer et al., *Brain Research*, 454, pp. 179–87 (1988). Appropriate choice of the molecular weight cut-off for the permselective channels will allow retention of laminin (a high molecular weight glycoprotein) within the nerve guidance channel. Similarly, blood vessels located in the proximal nerve stump may supply high molecular weight serum molecules such as fibronectin or glycoproteins that have supported neuronal survival and neurite extension in vitro. Aebischer et al., *Brain Research*, 454, pp. 179–87 (1988).

The nerve guidance channels of the present invention include an implantable, biocompatible tubular permselective membrane having openings to receive the severed nerve. The lumen of the membrane preferably has a diameter ranging from about 0.5 mm to about 2.0 cm, to permit the nerve to regenerate through it. The thickness of the membrane may range from about 0.05 to about 1.0 mm. In some embodiments the membrane has a molecular weight cut-off of about 100,000 daltons or less. The membrane is preferably impermeable to fibroblasts and other scar-forming connective tissue cells. Additionally, the membrane may be composed of a biodegradable material. An agarose matrix is disposed in the lumen of the nerve guidance channel. The agarose concentration should range between 0.5 to 1.25%, preferably 1.0%. The average gel pore radius can vary between 120 to 290 nm, and is most preferably approximately 150 nm.

The optimal concentration of agarose gel for use as a regeneration matrix will vary according to the intended use of the matrix. The optimal concentration for in vitro use may not be optimal for the in vivo milieu. Neurite outgrowth in agarose gels is strongly dependent upon the pore size of agarose gels. Syneresis at the channel mid-point could alter the pore size of agarose gels enough to inhibit regeneration and therefore result in the absence of nerve cable in the mid-portion of the regenerated nerve bundle. It is important to account and if possible, correct for syneresis of the gel at channel mid-point. This may be overcome by two strategies. One, the use of more dilute agarose gels to fill the channels may accommodate syneresis in the middle and still retain the pore size of gel at the channel midpoint to ranges permissible for neurite extension. Second, the use of a rough inner membrane of the channel may serve to prevent the fibroblast induced syneresis of the gel inside the guidance channel (Aebischer et al., *Brain Research*, 531, pp. 21–18 (1990)).

In one method of repairing a severed nerve according to this invention, the cut ends of the nerve are placed in proximity with each other within the lumen of the tubular guidance channel. The cut ends of the nerve are gently drawn into the channel by manual manipulation or suction. The nerve ends may be secured in position without undue trauma by sutures, or using a biocompatible adhesive, e.g., fibrin glue, or by frictional engagement with the channel.

In addition to the agarose matrices of the present invention, the lumen of the channel may be "seeded" with a substance that protects, nurtures, and/or enhances nerve growth therethrough. Useful substances include biologically active factors, such as nerve growth factors, brain derived growth factor, basic fibroblast growth factor, acidic fibroblast growth factor, or active fragments thereof. Alternatively, the lumen may be seeded with nerve-associated glial cells, such as Schwann cells. These growth factor cells and other nutrients may be provided within the nerve guidance channel as described supra.

The bioartificial ECMs of this invention may also carry one or more of the several cell adhesion molecules that have been identified to play an important role in cell migration and neurite extension in the developing nervous system, including N-CAM, Ng-CAM (Crossin et al., *Proc. Natl. Acad. Sci.*, 82, pp. 6942–46; Daniloff et al., *J. Neurosci.*, 6, pp. 739–58 (1986); tenascin (Wehrle et al., *Development*, 1990, pp. 401–15 (1990) and L1 (Nieke et al., *Differentiation*, 30, pp. 141–51 (1985).

Other useful factors include cAMP, or analogs thereof, including 8-bromo cAMP or chlorophenythio cAMP. See, e.g., U.S. Pat. Nos. 5,030,225 and 5,011,486.

The nerve guidance channels of this invention may additionally be seeded with Schwann cells. Schwann cells resident in the peripheral nerve trunk play a crucial role in the regenerative process. Schwann cells seeded in permselective synthetic guidance channels support extensive peripheral nerve regeneration. Schwann cells secrete laminin, which possesses neurite-promoting activity in vitro. See, e.g., Aebischer et al., *Brain Research*, 454, pp. 179–87 (1988). The Schwann cells are preferably longitudinally oriented along the guidance channel. This can be achieved by thermal manipulation of the agarose gel to orient the pores longitudinally, using methods well known in the art.

Insulin-like growth factor 1 (IGF-1) may also be useful in increasing the rate of regeneration of transected peripheral nerves and to decrease the persistence of permanent nerve function deficiency. See, e.g., U.S. Pat. No. 5,068,224.

Preferably the permselective membrane is fabricated to be impermeable to some of these substances so that they are retained in the proximity of the regenerating nerve ends. See, e.g., Aebischer, U.S. Pat. No. 5,011,486.

Briefly, various polymers and polymer blends can be used to manufacture the nerve guidance channel. Polymeric membranes forming the nerve guidance channel may include polyacrylates (including acrylic copolymers), polyvinylidenes, polyvinyl chloride copolymers, polyurethanes, polystyrenes, polyamides, cellulose acetates, cellulose nitrates, polysulfones, polyphosphazenes, polyacrylonitriles, poly(acrylonitrile/covinyl chloride), as well as derivatives, coplymers and mixtures thereof.

The membranes used in the nerve guidance channels of this invention may be formed by any suitable method known in the art. One such method involves coextrusion of a polymeric casting solution and a coagulant as described in Dionne, WO 92/19195 and U.S. Pat. Nos. 5,158,881, 5,283, 187 and 5,284,761, incorporated herein by reference.

The jacket may have a single skin (Type 1, 2), or a double skin (Type 4). A single-skinned hollow fiber may be produced by quenching only one of the surfaces of the polymer solution as it is co-extruded. A double-skinned hollow fiber may be produced by quenching both surfaces of the polymer solution as it is co-extruded. Typically, a greater percentage of the outer surface of Type 1 hollow fibers is occupied by macropores compared to Type 4 hollow fibers. Type 2 hollow fibers are intermediate.

The jacket of the nerve guidance channel will have a pore size that determines the nominal molecular weight cut off (nMWCO) of the permselective membrane. Molecules larger than the nMWCO are physically impeded from traversing the membrane. Nominal molecular weight cut off is defined as 90% rejection under convective conditions. Typically the MWCO ranges between 50 and 200 kD, preferably between 50 and 100 kD.

A preferred nerve guidance channel according to this invention for promoting regeneration of peripheral nerves across large gaps, includes an agarose matrix optimized in the regeneration environment to suit the re-growth of a particular nerve, the presence of Schwann cells seeded in the lumen of the channel, and the local release of growth factors from the wall of the guidance channel.

In one embodiment, agarose hydrogels are used as a carrier to present the laminin derived oligopeptide CDPGYIGSR (CysAspProGlyTyrIleGlySerArg; SEQ ID NO:1) to the site of nerve injury in an attempt to enhance nerve regeneration. Dorsal root ganglia have been shown to be responsive to CDPGYIGSR (CysAspProGly TyrIleGly-SerArg; SEQ ID NO:1) in vitro and show the greatest enhanced neuritic spread and neurite outgrowth compared to other fragments derived from laminin.

Compared to the ventral roots, transected dorsal roots have a limited regeneration through polymeric guidance channels across a nerve gap of 4 mm in adult rats after 4 weeks. McCormack et al., *J. Comp. Neurol.*, 313, pp. 449–56 (1991). Rat hind limb sural nerves have been shown to contain mainly sensory nerves with only 5% to 10% motor fibers Peyronnard et al., *Muscle and Nerve*, 5, pp. 654–60 (1982). Dorsal root and sural nerve transection enables comparison of regeneration between a sensory nerve cable close to the central nervous system, i.e., dorsal root, and one that is more peripheral, i.e., the sural nerve.

In order that this invention may be better understood, the following examples are set forth. These examples are for purposes of illustration only, and are not to be construed as limiting the scope of this invention in any way.

EXAMPLES

EXAMPLE 1

Characterization of Agarose Hydrogel Matrices

E14 Striatal Cell Assay

Striata were removed from 14-day-old rat embryos and mechanically dissociated with a fire-narrowed Pasteur pipette in serum-free medium. Different concentrations of agarose gels in the range of 0.5% to 5.0% were made in phosphate buffered saline pH 7.4. Gel solutions were sterilized by passing them through sterile 0.2 micron filters. Isolated E14 striatal cells were mixed into the gel solutions at room temperature in 1 ml syringes, each containing 300 µl of appropriate agarose gel concentration. The cell-gel solution mixture was then decanted into 48 well Costar tissue culture dishes. The dishes were cooled to 4° C. for the cell-gel solution mixture to gel, suspending the striatal cells in 3-D. One ml of a 1:1 mixture of DMEM and F12 nutrient (Gibco) supplemented with 5% fetal calf serum, glucose (33,M), glutamine (2mM), sodium bicarbonate (3 mM), HEPES buffer (5 mM, pH 7.4), insulin (25 µg/ml), transferrin (100 µg/ml), putrescine (60 µg/ml), progesterone (20 nM) and sodium selenite 30 nM) (all from Sigma) was added to the top of the gels. The gels were cultured in an incubator at 37° C. in 95% air, 5% $CO_2$ and 100% humidity. Striatal cells were also suspended in 100% Matrigel® at 4° C. and quickly decanted into 48 well Costar dishes and cultured in the manner describes above.

The percent striatal cells expending neurites of every 500 cells suspended in 3-D was measured for the agarose gel range of 0.5% to 5.0% (wt/vol) at 24, 48 and 72 hours in culture. Neurite extension was observed under light microscopy using a Zeiss Axiovert MC100 phase inversion microscope. All neurites whose length was greater than twice the striatal cell body diameter were counted.

E14 striatal cells extended neurites in 3-D in 1% agarose gels. Neurite extension from E14 striatal cells in 1% agarose gels was comparable to neurite extension in 100% Matrigel® after 72 hours in culture. E14 striatal cells extended neurites in the 0.5% to 1.25% gel range but did not extend neurites above a threshold concentration of 1.25% (wt/vol).

Chick dorsal root ganglion assay

Dorsal root ganglia were dissected from E9 chick embryos by a standard protocol. Chick embryos were immobilized in a prone position and a 3 mm long incision made on either side of the spine exposed DRGs for explanation. The DRGs were added to a 300 µl solution of 1% agarose in a 1ml syringe at room temperature, mixed gently and decanted into custom-built 9×9 mm cube shaped glass culture dishes. The 9×9 mm dishes were then placed at 4° C. for agarose to gel, trapping DRGs in 3-D. The cubic glass dish enables visualization of the X-Z axis, which is the plane perpendicular to the bottom of the culture dish. Three hundred microliters of 1% Ag-Plain gel solution was drawn into a 1 ml syringe, and the DRGs added to the gel solution with a micropipette. The ganglion-gel solution mixture was then decanted into the 9×9 dishes and cooled at 4° C. for 5 min, trapping the DRGs in the gel. Each well had two DRGs suspended int it. One ml of DMEM/F12 medium (Gibco) containing 10 ng/ml 2.5 s nerve growth factor (Sigma), glucose (0.3%), penicillin-streptomycin (1%), L-glutamine (200 mM), KCl (1.5 mM), insulin (0.08 mg/ml), transferring (10 mg/ml), putrescine (6 mM), and 5% fetal calf serum was added to the top of the gels. The cultures were maintained in an incubator at 37° C. with 100% humidification, 95% air and 5% $CO_2$. The cubic glass dish was flipped on its side after 6 days in culture, exposing the X-Z axis for analysis with light microscopy.

For neurite extension analysis along the X-Y axis, which is the plane parallel to the bottom of the culture dish, DRGs were suspended in plain agarose, agarose-GRGDSP (GlyArgGlyAspSerPro; SEQ ID NO:2), agarose-CDPGYIGSR (CysAspProGlyTyrIleGlySerArg; SEQ ID NO:1), agarose-x-IKVAV(IleLysValAlaVal; $AA_{11}$–$AA_{15}$ of SEQ ID NO:3)-x, agarose-PEPMIX and agarose-GGGGG (GlyGlyGlyGlyGly; SEQ ID NO:4) gels in standard 48 well Costar tissue culture dishes in the manner described above for the cubic glass culture dishes. At least 6 ganglia were analyzed for each type of agarose gel. The final concentration of the cell-gel solution mixture was 0.83% (wt/vol) and the total cell-gel volume in each culture well was 300 microliters.

Chick DRGs extended neurites in 1% agarose gels in both the X-Y and X-Z planes when cultured in the custom designed 9×9 mm glass cubic dishes after 6 days in the presence of NGF. DRGs extended long and tortuous neurites along the X-Y axis and the X-Z axis demonstrating the 3-D nature of neurite extension in agarose gels.

Gel Characterization a. Hydraulic permeability: Gel blocks of different concentrations, each of thickness 0.5 cm and radius 1 cm, were mounted on a custom-built water column. Each block was subjected to a known hydraulic pressure, typically a 100 cm high $H_2O$ column yielding approximately 24525 dynes/$cm^2$. The hydraulic permeability per unit time for a given hydraulic pressure was measured for the various gel concentrations. The average pore radius of the gel concentration range 0.5% to 5.0% was calculated as described by Refojo et al., *J.Appl.Poly.Sci.*, 9, pp. 3417–26 (1965) using the hydraulic permeability.

The average pore radius, calculated from the hydraulic permeability measurements of the various agarose gels, decreased exponentially as the gel concentration increased (FIG. 1). E14 striatal cells did not extend neurites beyond a threshold agarose gel pore radius of 150 nm. The slope of the curve depicting pore radius was steep between gel concentrations of 1% and 2% indicating a strong dependence of pore size on gel concentration.

b. Scanning Electron microscopy (SEM): Agarose gels in the range 0.5% to 2.0% were freeze-dried, mounted on aluminum stubs, coated with gold and analyzed under a Joel 35M scanning electron microscope. Representative sections of the scanning electron micrographs were selected for evaluating the morphology and size of the pores.

Scanning electron micrographs of different concentrations of agarose gels revealed an open-cell morphology.

c. Electron microscopy (ESEM): Agarose gels of the concentration range 0.5% to 2.5% were analyzed with an environmental scanning electron micrograph (Electroscan ESEM, type E3) under partially hydrated states to qualitatively asses gel pore morphology.

A decline in gel cavity radius was noted with increasing gel concentration. However, the nature and quality of images obtained with the ESEM allowed only qualitative conclusions on gel pore size to be drawn with confidence.

d. Gel electrophoresis: The electrophoretic mobility of insulin (Mw 5,700), bovine serum albumin (Mw. 66,000; radius 140 Angstroms) and bovine thyroglobulin (Mw. 669, 000) in 1%, 2% and 4% agarose gels was measured under a constant electrophoretic voltage gradient. Twenty ml of the appropriate agarose gel concentration was poured into a DANAPHOR model 100 mini gel electrophoresis apparatus (Tectate S.S, Switzerland) with platinum electrodes. The proteins insulin, albumin and thyroglobulin were then subjected to a constant electrophoretic voltage gradient of 1 to 12 V. The protein electrophoretic mobility was measured in the 1%, 2% and 4% agarose gels by measuring distance traveled per unit time. The relative electrophoretic velocity was then calculated after taking into account the isoelectric points of the different proteins, the voltage employed and the time of exposure to enable electrophoretic mobility comparisons of insulin, albumin thyroglobulin in the agarose gels.

The relative electrophoretic mobility of the globular proteins insulin, albumin and thyroglobulin, fell with increasing gel concentration. The electrophoretic mobility of insulin and albumin decreased by relatively small percentage in 2% agarose gels compared to 1% gels i.e., by 5.7% and 2.9% respectively. In contrast, the relative electrophoretic mobility was attenuated by 33.3% in 2% agarose gels relative to that in 1% agarose gels for the large molecular weight globular protein, bovine thyroglobulin.

Laminated Gels

A 3 mm thick, cell-free layer of non-permissive 2% agarose gel solution, a 1 mm layer of permissive 1% gel solution with chick DRGs mixed in it, and an additional 3 mm, cell-free layer of non-permissive 2% agarose solution were serially cooled and gelled in a custom designed 9×9 mm cubic glass dishes. The dishes were then turned on their side exposing the X-Z axis and analyzed under light microscopy after 6 days in culture. The gel interfaces were examined for neurite cross-over from one gel layer to the other.

Chick DRGs suspended in the permissive 1% agarose gel layer extended neurites only in the 1% gel and did not cross-over the 1%:2% gel interface. In comparison, many neurites were able to cross-over a control gel interface of 1%:1W agarose gel. By experimental design, all the neurites encountering the interfaces were extending in the X-Z axis of the gel, perpendicular to the bottom of the culture dish.

EXAMPLE 2

A Bioartificial ECM of Oligopeptide-derivatized Agarose

Preparation of Agarose Gels

One percent (wt/vol) hydroxyethylated agarose (SeaPrep®, FMC Corp. Rockland, Me.) gels were prepared by dissolving agarose in phosphate buffered saline (PBS) at pH 7.4. The gel solutions were passed through a 0.2 micron filter for sterilization. Gel solutions were then placed at 4° C., allowed to gel, and stored at 4° C. until they were derivatized with peptides.

Immobilization of Laminin Oligopeptides

Agarose gels were derivatized with 1,1 carbonyldiimidazole (CDI) (Sigma) using a modified version of the protocol described by Hearn, *Methods Enzymol.*, 135, pp. 102–17 (1987). See FIG. 2 for schematic. Three to four ml gel blocks of 1 agarose were dehydrated by repeated washes in acetone followed by acetone which was dried under 4 Angstrom molecular sieves (Sigma). A 150 mg/25 ml CDI solution prepared in dry acetone was added to the acetone washed agarose gels (5 ml/3 g gel block). The activation reaction was allowed to proceed for 9 min with gentle agitation. Gels were then washed five times with dry acetone for 6 min per wash to remove unbound CDI.

CDI activated gels were then exposed to various oligopeptides dissolved in 100 mM sodium bicarbonate buffer solution at pH 8.5 at a concentration of 0.6 mg/ml. Peptide coupling reaction was allowed to proceed for 36 hr under gentle agitation.

The gels were then washed thoroughly with PBS for 48 hr, further quenched in sodium bicarbonate for 2 hr at room temperature, lyophilized and re-dissolved to the desired gel concentration of 1.00%.

The peptides used were GRGDSP (GlyArgGlyAspSerPro; SEQ ID NO:2) (Telios pharmaceuticals, San Diego Calif.), CDPGYIGSR (CysAspProGlyTyrIleGlySerArg; SEQ ID NO:1), the 19-mer sequence CSRARKQAASIKVAVSADR (CysSerArg AlaArgLysGlnAlaAlaSerIleLysValAlaValSerAlaAspArg; SEQ ID NO:3), an x-IKVAV-x containing sequence (x-IleLysGValAlaVal-x; $AA_{11}$–$AA_{15}$ of SEQ ID NO:3) (Anawa, Wagen, Switzerland) and as a control, GGGGG (GlyGlyGlyGlyGly; SEQ ID NO:4) (Sigma). A cocktail of the three aforementioned peptides (PEPMIX) was also immobilized to the hydrogel backbone at a concentration of 2 mg each in a total of 5 ml buffer solution.

The 1'1 carbonyldiimidazole coupling reaction used for immobilizing peptides to the agarose gels was verified by binding radiolabelled $^{14}C$ glycine as a model amino compound for the various peptides. Gels which were not activated with CDI, but exposed to 14C glycine were used as controls. Beta counts from CDI activated and CDI deficient gels were counted with a β counter (LKB Wallac, 1217 RackBeta liquid scintillation counter) after dialyzing for 12 days.

CDPGYIGSR (CysAspProGlyTyrIleGlySerArg; SEQ ID NO:1) was labelled with $^{125}I$ using lactoperoxydase (Sigma). Ten µl of CDPGYIGSR (CysAspProGlyTyrIleGlySerArg; SEQ ID NO:1) solution in 0.4M sodium acetate solution ($^5$ µg/10 µl of sodium acetate), 1 millicurie of 125I (Amersham Radio Chemicals) and 10 µl of hydrogen peroxide ($H_2O_2$; 1 in 20,000 parts). The reaction was allowed to proceed for 1 min and stopped with 500 µl of 0.1M sodium acetate solution.

Radiolabelled CDPGYIGSR (CysAspProGlyTyrIleGlySerArg; SEQ ID NO:1) was eluted with 20% to 50% methanol in an octodesasilicic acid (ODS) gel column (Shandon Scientific Ltd., Cheshire England). $^{125}I$ CDPGYIGSR (CysAspProGlyTyrIleGlySerArg; SEQ ID NO:1) was coupled to agarose gels in the manner described above. Gamma counts were analyzed with a Packard autoscintillation spectrometer (5416) after 5 days of washing to remove unbound peptide.

Beta counts of $^{14}C$ glycine bound to CDI derivatized agarose revealed that up to 37 µg of glycine was retained per gm of gel after 12 days of dialysis. CDPGYIGSR (CysAspProGlyTyrIleGlySerArg; SEQ ID NO:1) was successfully radiolabelled with $^{125}$I and the peak elution is ODS gels was the 40% methanol. In the presence of CDI, 2.39 times more $^{125}$I labeled CDPGYIGSR (CysAspProGlyTyrIleGlySerArg; SEQ ID NO:1) was retained in agarose gels compared to gels without CDI after 5 days of dialysis of the gel. The short half-life period of 125I prevented further washing even though the gamma counts in the CDI deficient gel were failing more rapidly with each successive wash compared to the counts in CDI activated agarose gel.

Gel Characterization

Gel porosity of underivatized agarose gels and glycine coupled agarose was determined as described in Example 1. The average pore radius of the gels were determined to be 310 nm for a 0.5% underivatized agarose gel and 360 nm for a 0.5% glycine coupled agarose gel using the water column for hydraulic permeability measurements.

Dorsal Root Ganglion Assay

DRGs were dissected from E9 chick embryos by a standard protocol, as described in Example 1.

Neurite extension was analyzed qualitatively along the X-Y axis using a Zeiss axiovert MC100 TV light microscope at days 2, 4 and 6. Cell viability of both cell types was assessed by a fluorescein diacetate (FDA) assay at day 6. For the DRG study, the ganglionic cell body area (GCBA), and the total ganglionic spread area (TGSA) defined as the maximum area covered by the ganglion and its neurites, were measured in the X-Y plane using an NIH Image 1.47 software package. The ratio of TGSA/GCBA, defined as the total neuritic spread of the ganglia, was calculated. The length of five of the longest neurites extended by the DRGs was also measured to assess neurite extension.

Agarose hydrogels supported neurite outgrowth from DRGs in both X-Y and X-Z planes, demonstrating the 3-D character of neurite outgrowth in agarose gels. Fluorescein diacetate assay showed viable DRG neurons after 6 days in culture in all agarose gels used.

DRG neurons extended neurites in all of the agarose gels when examined in the X-Y plane in 48 well Costar dishes including Ag-Plain and Ag-CDPGYIGSR (CysAspProGlyTyrIleGlySerArg; SEQ ID NO:1).

Figure 3:
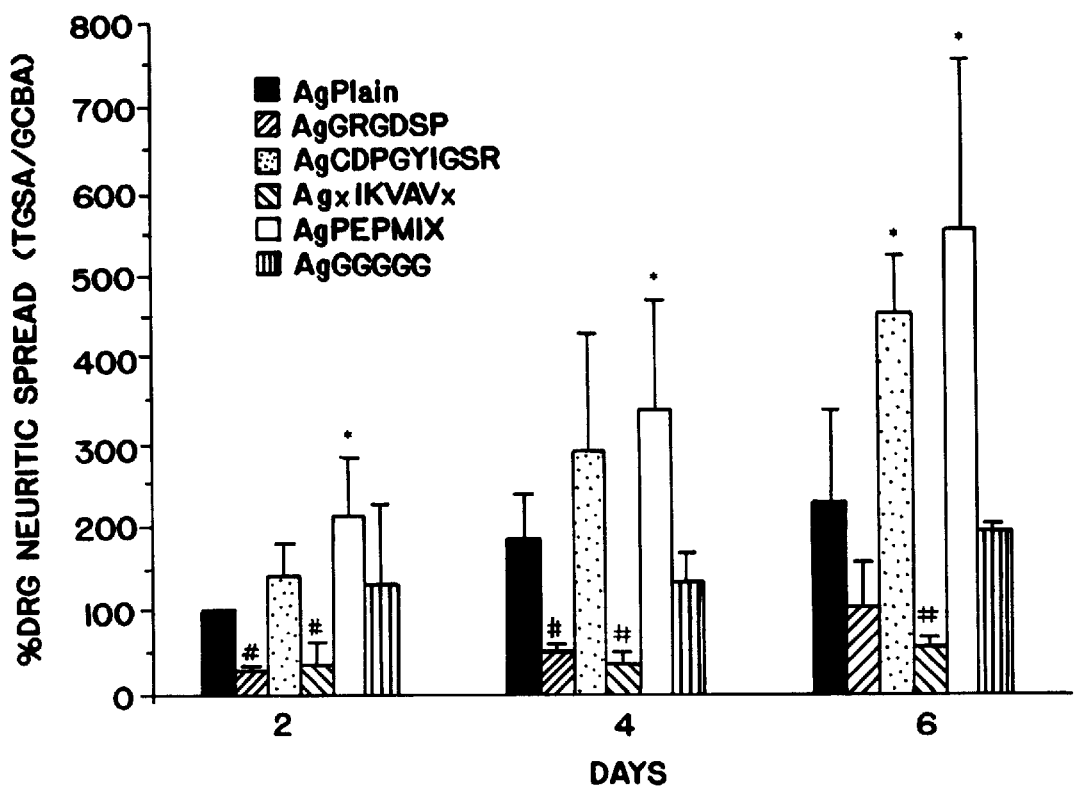
FIG. 3. Histogram depicting E9 chick DRG neuritic spread as the ratio of total ganglionic spread area/ganglionic cell body area (TGSA/GCBA). Neuritic spread in various gels is plotted as a percentage of neuritic spread in Ag-Plain gels at 2 days (n=6). Error bars represent standard deviation. '*' depicts a statistically significant higher neuritic spread ($p<0.05$) relative to Ag-Plain; '#' depicts a statistically significant lower neuritic spread ($p<0.05$) relative to Ag-Plain.

The total ganglionic spread area/ganglionic cell body area ratio (TGSA/GCBA) was calculated at days 2, 4 and 65 to account for the variance in the size of the dorsal root ganglia after dissection and as a measure of the total neuritic spread in the gels (FIG. 3). Compared to AgPlain gels, Ag-PEPMIX gels showed significantly greater neuritic spread at all measured time points (p<0.05) while CDPGYIGSR (CysAspProGlyTyrIleGlySerArg; SEQ ID NO:1) had significantly greater neuritic spread only at day 6 (p<0.05). In contrast, IKVAV-derivatized (IleLysValAlaVal; $AA_{11}$–$AA_{15}$ of SEQ ID NO:3) gels had significantly lesser neuritic spread at all measure time points while GRGDSP (GlyArgGlyAspSerPro; SEQ ID NO:2) had significantly lower neuritic spread only at days 2 and 4 (p<0.05), compared to AgPlain gels at all measured time points.

Figure 4:
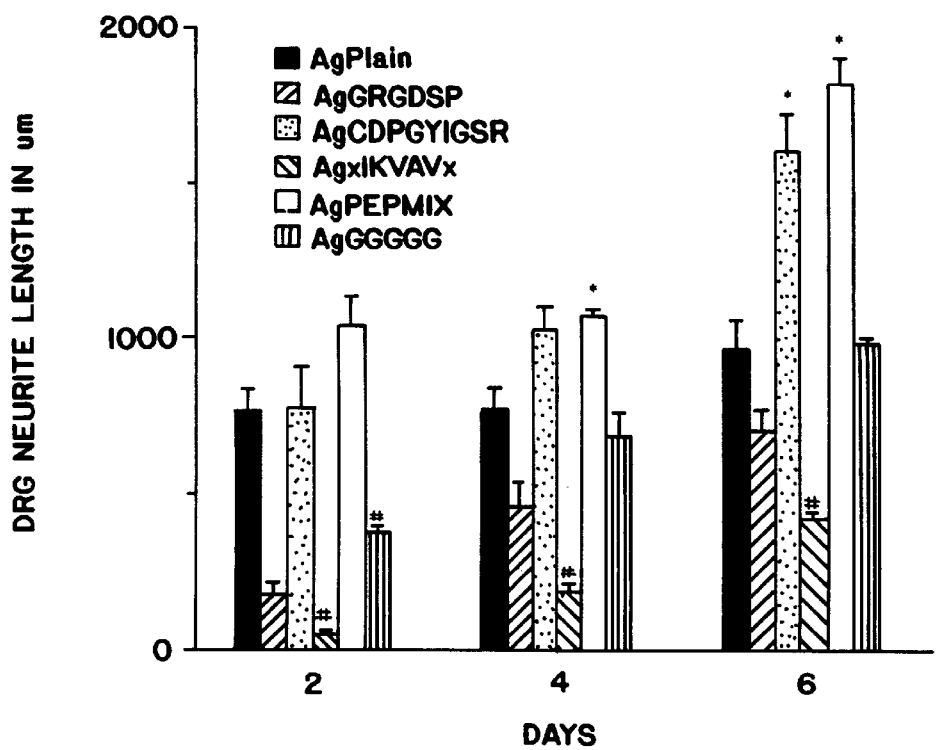
FIG. 4. Histogram of comparative E9 Chick DRG neurite extension in underivatized and derivatized agarose gels (n=6). Error bars represent standard deviation. '*' denotes a statistically significant, higher neurite length ($p<0.05$) compared to Ag-Plain; '#' denotes a statistically significant lower neurite length ($p<0.05$) compared to Ag-Plain.

CDPGYIGSR (CysAspProGlyTyrIleGlySerArg; SEQ ID NO:1) and PEPMIX derivatized agarose gels supported significantly longer neurites than underivatized agarose gels (p<0.05) at day 6 (FIG. 4). In contrast, IKVAV-derivatized (IleLysValAlaVal; $AA_{11}$–$AA_{15}$ of SEQ ID NO:3) agarose gels inhibited neurite outgrowth at days 2, 4 and 6 (p<0.05). Ag-GGGGG (GlyGlyGlyGlyGly; SEQ ID NO:4) gels had a significantly lower (p<0.05) neurite length compared to Ag-Plain at day 2 but there was no statistical difference in neurite length between the two gels at days 4 and 6. In all the agarose gels, neurites extended three dimensionally including the X-Z plane. The neurites were long and tortuous, extending up to 1600 microns at day 6 in CDPGYIGSR-derivatized (CysAspProGlyTyrIleGlySerArg; SEQ ID NO:1) gels.

PC12 Cell Assay

PC12 cells (American Type Culture Collection, Rockville, Md.) were grown in Gibco's RPMI 1640 with 10% fetal calf serum, 5% horse serum, L-glutamine (200 mM) and 1% penicillin-streptomycin. They were primed at the tenth passage with 10 ng/ml 2.5 s nerve growth factor (NGF) for 48 hr prior to use. Primed PC12 cells were then mixed in the various agarose gel solutions at a density of 50,000 cells per ml using a method similar to the one described above for DRGs. The cell-gel solution mixtures were poured into 48 well Costar tissue culture dishes and allowed to gel by cooling 4° C. One ml of PC12 medium was added to the tope of the gels along with 10 ng/ml of NGF. The cultures were placed in an incubator at 37° C. with 100% humidification, 93% air and 7% $CO_2$.

The percentage of PC12 cells extending neurites in the various agarose gels was assessed by selecting optical cylindrical sections of the gels for analysis at a magnification of 200× under light microscopy. Optical cylindrical sections were chosen by serially moving the microscope visual field from the center of the dish to the side along parallel paths. At least nine hundred PC12 cells were examined for neurite extension in each well and at least 6 wells of each type of agarose gel were analyzed. The inclusion criterion for a positive count was a neurite longer than on PC12 cell body diameter. Two sided Student t-test was employed to determine statistical significance with p<0.05 considered to be significant.

Figure 5:
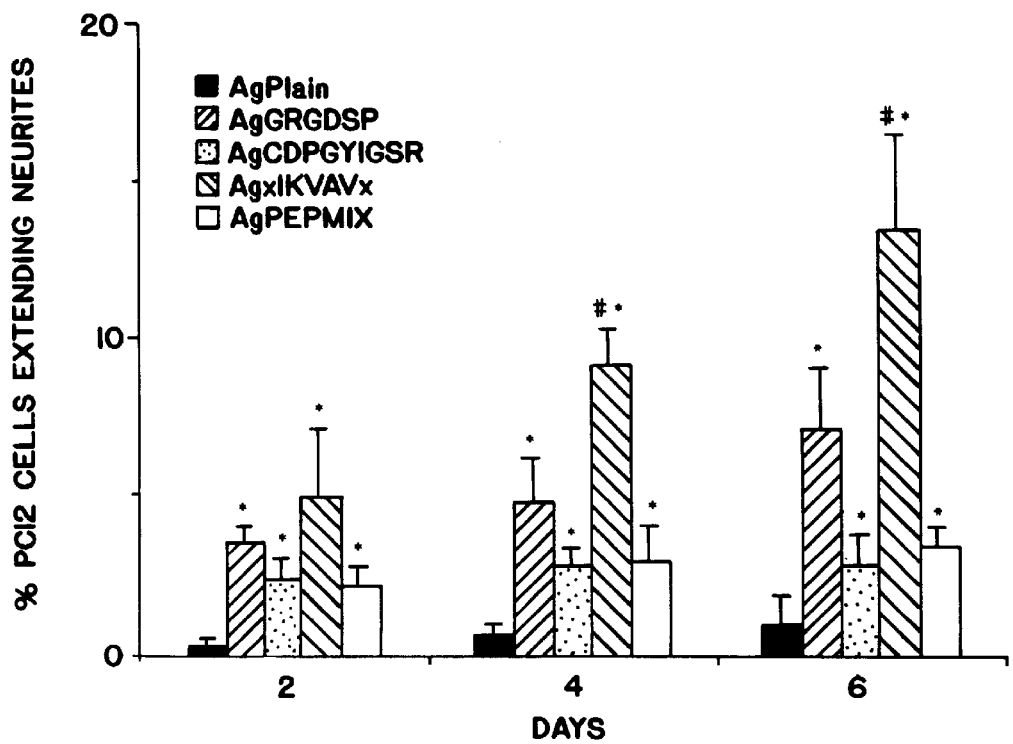
FIG. 5. Histogram depicting comparative PC12 neuritic extension in underivatized and derivatized agarose gels (n=6). Error bars represent standard deviation. '*' depicts a significant difference with respect to Ag-Plain ($p<0.05$); '#' depicts a significant difference with respect to all other LN oligopeptide derivatized agarose gels ($p<0.05$).

PC 12 cells were viable as evidenced by an FDA assay in all gels except Ag-GGGGG (GlyGlyGlyGlyGly; SEQ ID NO:4). PC12 cells also extended neurites in all gels after 6 days in culture except in Ag-GGGGG (GlyGlyGlyGlyGly; SEQ ID NO:4) gels. However, the percent PC12 cells that extended neurites depended upon the type of gel used. At all measured time points, the laminin oligopeptide derivatized agarose gels supported significantly greater percent neurite extension (p<0.05) than underivatized Ag-Plain gel. Neuritic extension in Ag-x-IKVAV(IleLysValAlaVal; $AA_{11}$–$AA_{15}$ of SEQ ID NO:3)-x gels was significantly higher (p<0.05) compared to the Ag-GRGDSP (GlyArgGlyAspSerPro; SEQ ID NO:2), Ag-CDPGYIGSR (CysAspProGlyTyrIleGlySerArg; SEQ ID NO:1), Ag-PEPMIX and underivatized agarose gels at days 4 and 6 (FIG. 5).

In the absence of NGF, no neurite extension was observed in any of the agarose gels. No measurable difference in the neurite length was observed between the Ag-plain and the various derivatized agarose gels (data not shown). The overall percent of PC12 cells extending neurites in the various derivatized agarose gels, IKVAV-derivatized (IleLysValAlaVal; $AA_{11}$–$AA_{15}$ of SEQ ID NO:3) gels including, was lower than the percent cells extending neurites in 100% Matrigel® or 1.2 mg/ml Vitrogen® gels (36.5% and 32.8% respectively at 4 days).

EXAMPLE 3

The effect of derivatized agarose gels on the regeneration of transected rat spinal dorsal roots was evaluated by using 6 mm long polymer guidance channels filled with CDPGYIGSR (CysAspProGlyTyrIleGlySerArg; SEQ ID NO:1)—agarose to bridge a 4 mm gap in a transected dorsal root model. After 4 weeks, significantly greater numbers of myelinated axons were observed in the channels filled with CDPGYIGSR (CysAspProGly TyrIleGlySerArg; SEQ ID NO:1)—agarose gels compared to channels filled with underivatized agarose gels.

Guidance Channels

Guidance channels were fabricated from acrylonitrile-vinylchloride (PAN/PVC) copolymers by wet-jet wet spinning. Cabasso, I., In Encyclopedia of Chemical Technology, 12, pp. 492–517 (1978); Aebischer et al., Biomaterials, 12, pp. 50–56 (1991). The channel consisted of a smooth inner and outer skin with a molecular weight cut-off 50,000 Da, with an open trabecular network in between, which provided the structural support for the channel. Channels of internal diameter 0.8 mm and 0.5 mm were fabricated for the spinal root and sural nerve model respectively.

CDPGYIGSR Derivatized Agarose Gels

One percent (wt/vol) agarose gels were derivatized with LN oligopeptide CDPGYIGSR (CysAspProGlyTyrIleGlySerArg; SEQ ID NO:1) as described in Example 2. PAN/PVC guidance channels were sterilized by storing in 70% ethanol overnight. Guidance channels were filled with CDPGYIGSR (CysAspProGlyTyrIle GlySerArg; SEQ ID NO:1) derivatized and underivatized agarose gel solutions and the ends of the channel were sealed with heat to prevent leakage of gel solution. The channels were then cooled to 4° C. to allow agarose solutions to gel. After agarose solutions "gelled" inside the channels they were cut to a standard length of 6 mm and 10 mm for the dorsal root and sural nerve implants respectively.

Animal Model and Guidance Channel Implantation

Figure 6:
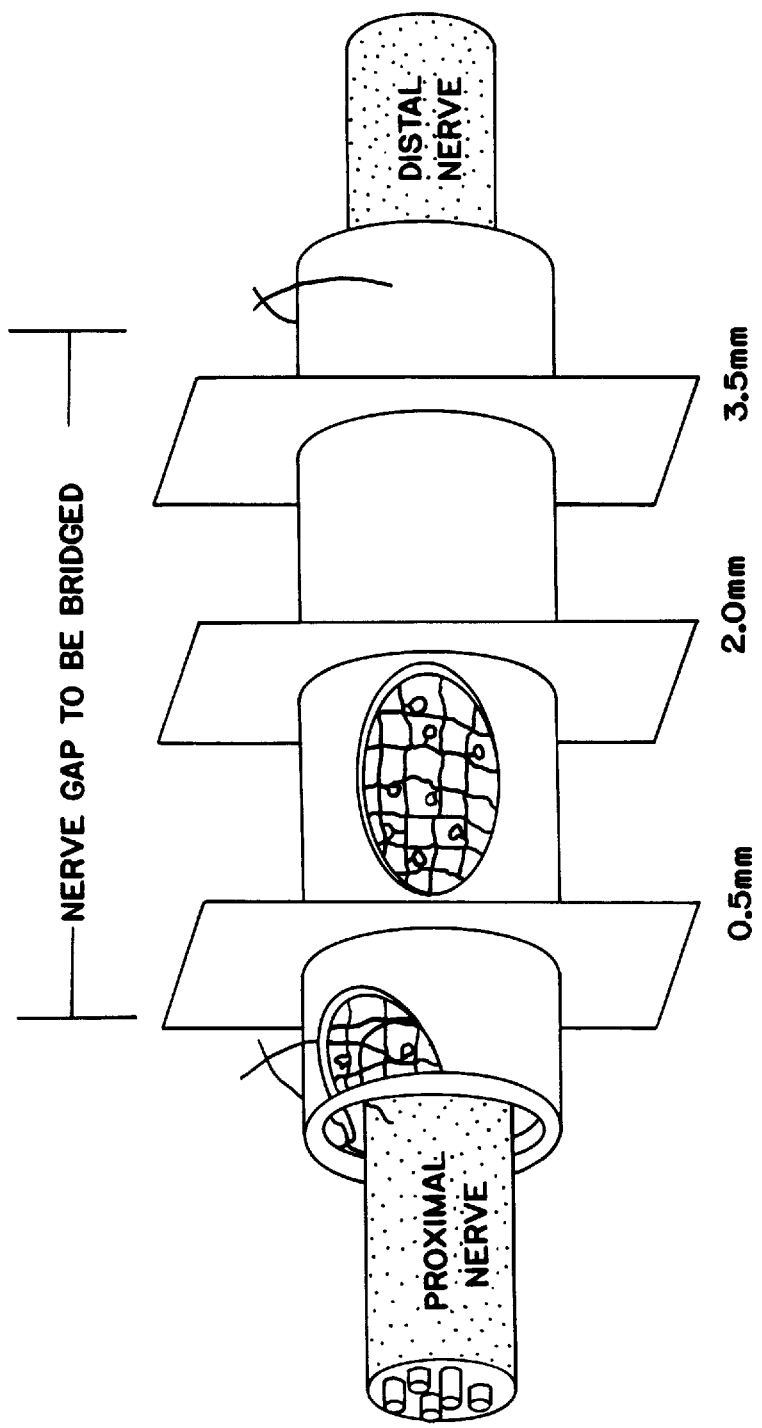
FIG. 6. Schematic illustration of dorsal root regeneration across a nerve gap of 4.0 mm with a nerve guidance channel whose lumen is loaded with agarose gel.

Adult male albino rats (Wistar) weighing 180 to 220 gm were anesthetized by an intraperitoneal injection of pentobarbital (60 mg/kg). The dorsal operative site was shaved and swabbed with an iodophore (Butadiene). A 5 mm dorsal midline incision was made using the iliac crests as landmarks. Retraction of paraspinous muscles exposed L2–L6 vertebrae. Bilateral laminectomies were performed on L2 to L5 to expose the spinal cord. The spinal roots were exposed by a midline incision on the dura mater. Using a blunt nerve hook the dorsal root exiting the L4 vertebra was identified and a 2 mm section removed. Six millimeter long guidance channels carrying underivatized agarose and CDPGYIGSR-derivatized (CysAspProGlyTyrIleGlySerArg; SEQ ID NO:1) agarose were used to bridge the 2 ends of the nerve using a 10-0 monofilament nylon suture (Ethicon) (see FIG. 6 for schematic). Five rats received channels filled with underivatized agarose and six animals received channels filled with CDPGYIGSR-derivatized (CysAspProGlyTyrIleGlySerArg; SEQ ID NO:1) agarose.

For the sural nerve model, the hind limb operative site was shaved and cleaned with iodophore. "L" shaped incisions were made on the left hind limbs of 180–220 g albino rats (Wistar) along and dorsal to the femur and continuing past the knee. The gluteus maximus muscle was retracted and the sciatic nerve was exposed. The sural branch of the sciatic nerve was identified, followed down beneath the knee joint, and a 2 mm long piece of the nerve was transected. The ends of the nerve were then bridged with guidance channels which were filled with either saline or underivatized agarose or CDPGYIGSR-derivatized (CysAspProGlyTyrIleGlySerArg; SEQ ID NO:1) agarose. Five animals received saline filled channels, five received agarose plain channels and four received CDPGYIGSR (CysAspProGly TyrIleGlySerArg; SEQ ID NO:1)—agarose filled channels. All animals were housed in an controlled environment with 12 hour on-off light cycles. They received food and water ad libitum.

Implant Retrieval and Evaluation

Four weeks post-implantation, the animals were deeply anesthetized with an intra-peritoneal injection of sodium pentobarbital and transcardially perfused with 200 ml of heparinized physiologic saline followed by 250 ml of a cold 4% paraformaldehyde 2.5% gluteraldehyde solution in phosphate buffered saline at pH 7.4. The operative site was reopened, and the guidance channel retrieved. The specimens were post-fixed, dehydrated and embedded in glycomethacrylate. The cable cross-sectional area, the number of myelinated axons at 1.5 mm, 2 mm and 3.5 mm of the dorsal root channel were analyzed with NIH software 1.47 interfaced with a Zeiss Axiovert MC100 microscope. The proximal nerve stump was defined to be at the 0 mm point and the distal nerve stump at the 4 mm point of the 4 mm nerve gap in dorsal roots. For the sural nerve implants, the cable cross-sectional area and the number of myelinated axons at 2 mm point along the channel was evaluated on 6 micron semi-thin sections. All sections were stained with osmium tetraoxide and cresyl violet.

Dorsal Root Regeneration

Figure 7:
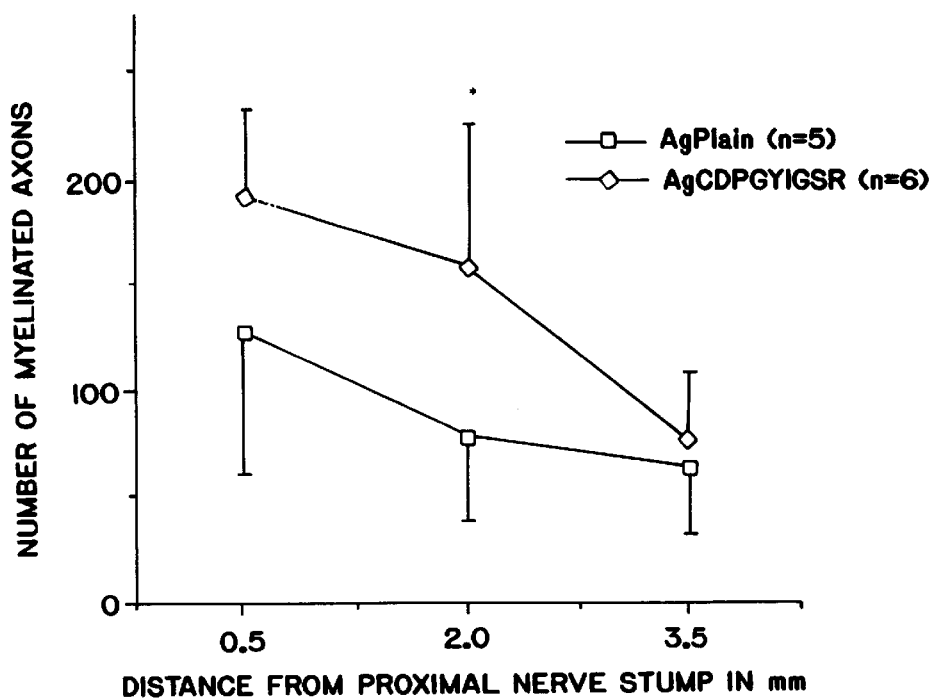
FIG. 7. Graph showing the number of myelinated axons regenerated at 4 weeks along polymer guidance channels filled with AgPlain and Ag-CDPGYIGSR (CysAspProGlyTyrIleGlySerArg; SEQ ID NO:1) gels. "*" depicts a statistically significant difference with $p<0.05$ using the Student t test.
Figure 8:
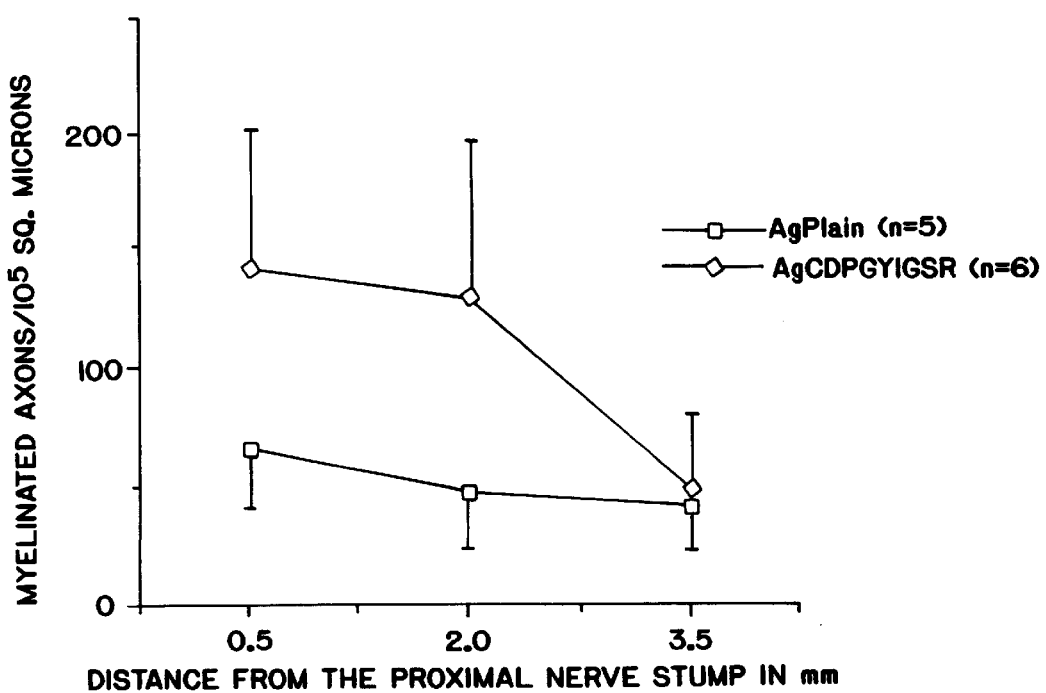
FIG. 8. Graph showing the density of yelinated axons regenerated at 4 weeks along polymer guidance channels filled with AgPlain and Ag-CDPGYIGSR (CysAspProGlyTyrIleGlySerArg; SEQ ID NO:1) gels. "*" depicts a statistically significant difference with $p<0.05$ using the Student t test.

Semi-thin cross-sections along the length of the guidance channel showed that myelinated axons were present all along the 4 mm nerve gap. Histological sections of guidance channels filled with agarose gels carrying regenerated dorsal roots showed doughnut shaped, centrally located nerve cables. Tissue reaction to the PAN/PVC polymer consisted of multi-nucleate giant cell and connective tissue infiltration. Neovascularisation was evident in the midst of regenerated nervous tissue along with Schwann cell infiltration. Light micrographs of regenerating dorsal root cables at 4 weeks post-implantation at the mid-point of guidance channels showed comparatively more nervous tissue in channels containing CDPGYIGSR (CysAspProGlyTyrIleGlySerArg; SEQ ID NO:1) gels relative to channels with underivatized agarose. At the mid-point of the 4 mm nerve gap, the channel filled with AgCDPGYIGSR (CysAspProGly TyrIleGlySerArg; SEQ ID NO:1) had a significantly greater (p<0.05) number of myelinated axons compared to the channels with agarose plain gels (see FIG. 7). The number of myelinated axons at the midpoint in the agarose plain filled channels were comparable to those in saline filled channels described by McCormack et al., J.Comp. Neurol., 313, pp. 449–56 (1991). CDPGYIGSR-derivatized (CysAspProGly TyrIleGlySerArg; SEQ ID NO:1) agarose gels had a significantly higher density (p<0.05) of myelinated axons at 0.5 mm and 2.0 mm along the channel at 4 weeks postimplantation (FIG. 8). The density of myelinated axons is defined as the number of myelinated axons per $10^5$ square microns of cable area.

Sural Nerve Regeneration

Figure 9:
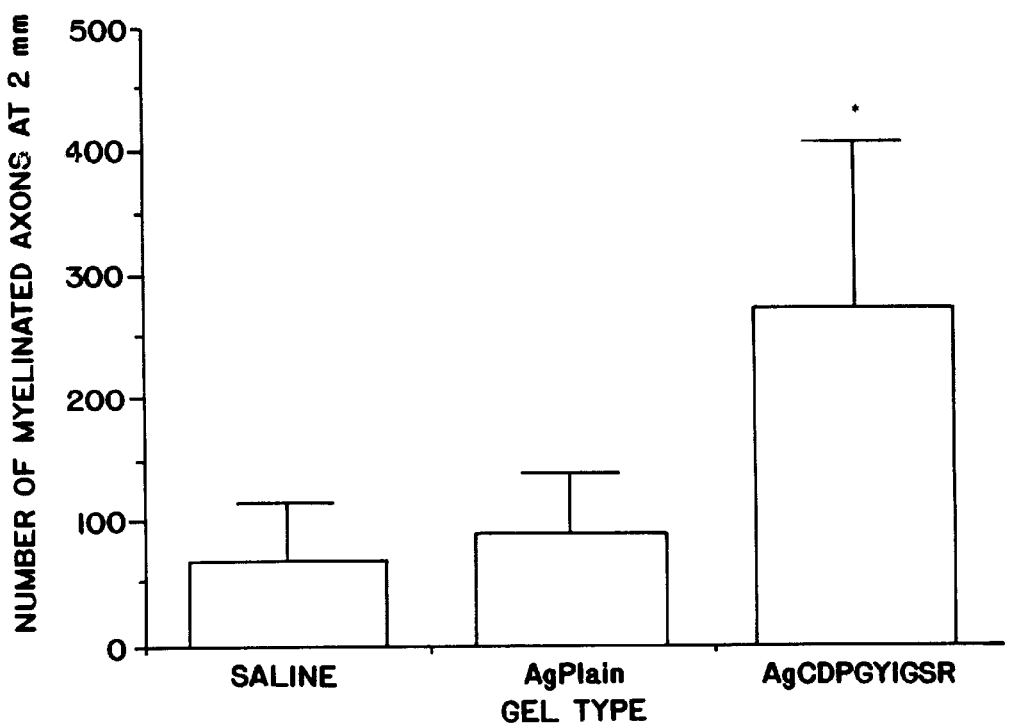
FIG. 9. Histogram depicting the number of myelinated axons in regenerating sural nerves at 2.0 mm distance from the proximal nerve stump in polymer guidance channels filled with A) saline; B) AgPlain and C) Ag-CDPGYIGSR (CysAspProGlyTyrIleGlySerArg; SEQ ID NO:1). "*" depicts a statistical difference of $p<0.05$ when compared to saline or AgPlain. Student t test was used to evaluate statistical significance.
Figure 10:
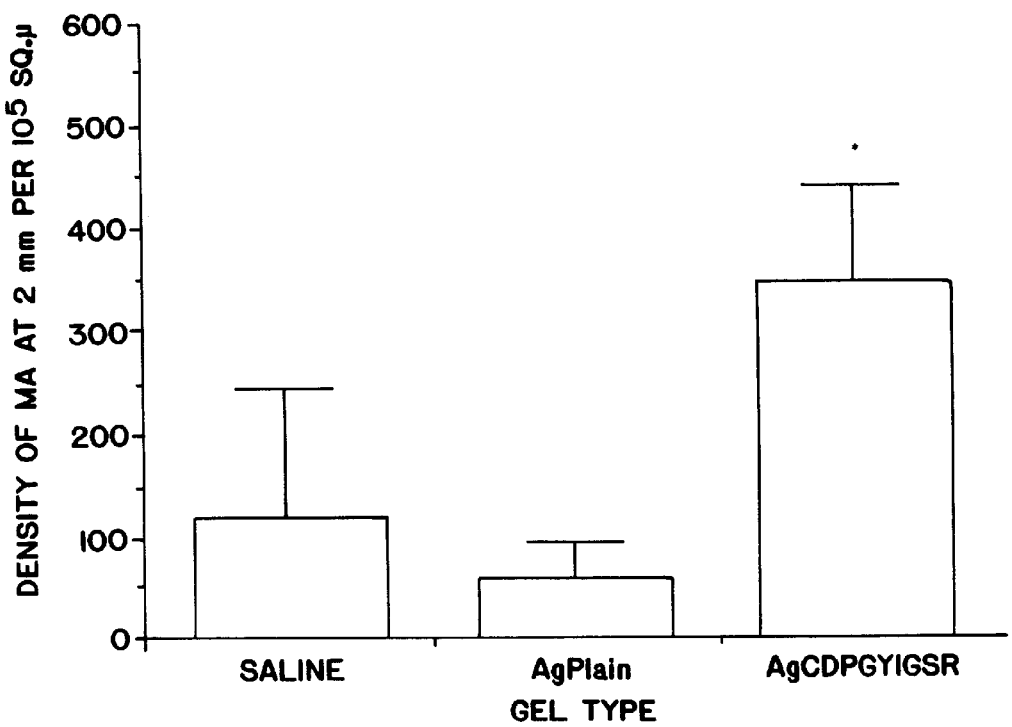
FIG. 10. Histogram depicting the density of myelinated axons in regenerating sural nerves at 2.0 mm distance from the proximal nerve stump in polymer guidance channels filled with A) saline; B) AgPlain and C) Ag-CDPGYIGSR (CysAspProGlyTyrIleGlySerArg; SEQ ID NO:1). "*" depicts a statistical difference of $p<0.05$ when compared to saline or AgPlain. Student t test was used to evaluate statistical significance.

All of the 10 mm long guidance channels implanted to bridge transected sural nerves were kinked due to flexion at the rats' knee-joint. Histological evaluation of nerves proximal to the kink showed regenerated cables located at the center of the channel with myelinated axons. All cables present in the channel distal to the kink contained a fibrotic cable but no myelinated axons. Almost all of the kinks occurred between 2–4 mm into the nerve gap. Therefore only the 2 mm point was analyzed for myelinated axons in this study. Light micrographs of regenerating sural nerves, 4 weeks post-implantation at the 2.0 mm point in polymer guidance channels filled Ag-CDPGYIGSR (CysAspProGlyTyrIleGlySerArg; SEQ ID NO:1) showed relatively higher numbers of nerve fascicles and neovascularization than in the other guidance channels. At 2 mm into the 8 mm nerve gap, guidance channels filled with AgCDPGYIGSR(CysAspPro GlyTyrIleGlySerArg; SEQ ID NO:1) gels had a significantly greater number (p<0.05) of myelinated axons compared to either the saline filled channels or agarose plain filled channels. See FIG. 9. At this point, the density of myelinated axons in the CDPGYIGSR-derivatized (CysAspProGlyTyrIleGlySerArg; SEQ ID NO:1) agarose channels was also significantly greater (p<0.05) than the density of axons in the agarose-plain and saline-filled channels (FIG. 10). When the number of myelinated axons was compared to the number present in a normal control sural nerve, at 4 weeks, the average number of myelinated axons regenerated across the saline filled channel was 12% of control sural nerve, 13% of control nerve for AgPlain filled channels and 40% of control sural nerve for AgCDPGYIGSR (CysAspProGlyTyrIleGlySerArg; SEQ ID NO:1) filled channels.

Transected rat dorsal roots regenerate across a 4 mm gap after 4 weeks in semipermeable guidance channels filled with agarose gels derivatized with LN oligopeptides. This is in contrast to the limited regeneration obtained by earlier experiments in the same model (McCormack et al., *J. Comp. Neurol.*, 313, pp. 449–56 (1991) using channels filled with saline only. Though there was no significant difference in the number of myelinated axons 0.5 cm into the nerve gap, channels filled with CDPGYIGSR (CysAspProGly TyrIleGlySerArg; SEQ ID NO:1) derivatized agarose gels had significantly greater myelinated axons at the mid point of the channel compared to channels filled with agarose plain. This observation suggests a faster rate of nerve regeneration in gels derivatized with the CDPGYIGSR (CysAspProGlyTyrIleGlySerArg; SEQ ID NO:1) compared to AgPlain gels.

The number of myelinated axons at the midpoint of the channel in underivatized agarose gels was comparable to the number obtained in the saline filled channels of McCormack. This demonstrates that agarose gels are not inhibitory to regeneration in semipermeable channels as some other matrices like Matrigel® have been shown to be. See, e.g., Valentini et al., *Exp. Neurol.*, 98, pp. 350–56 (1987). CDPGYIGSR (CysAspProGlyTyrIleGlySerArg; SEQ ID NO:1) derivatized agarose gels also have a higher density of myelinated axons in the regenerated cable compared to underivatized agarose gels at 0.5 and 2.0 mm nerve gap points. This observation coupled with the data on numbers of myelinated axons along the channel, indicates that there is lesser fibrotic tissue per cable area in the derivatized agarose gels compared to underivatized AgPlain gels.

The doughnut shape of the regenerated cable at the midpoint of the channel points to possible syneresis of the agarose gels due to cellular activity in the regeneration environment.

All of the 10 mm long guidance channels across the 8 mm sural nerve gap were kinked distal to the point 2 mm into the nerve gap because of the channel was located across the knee-joint of the rat. However, at the 2 mm point, both the number and density of myelinated axons were greater in channels filled with CDPGYIGSR-derivatized (CysAspProGlyTyrIleGlySerArg; SEQ ID NO:1) agarose compared to channels filled with underivatized agarose or saline.

Therefore in both the dorsal root model and in the more peripheral sural nerve model, CDPGYIGSR-derivatized (CysAspProGlyTyrIleGlySerArg; SEQ ID NO:1) agarose channels had greater numbers of myelinated axons in higher densities per cable area compared to channels filled with underivatized agarose or saline filled channels.

This data indicates the feasibility of developing a matrix designed to enhance nerve regeneration by coupling neurite promoting biomolecules to agarose hydrogels.

We claim:

1. A nerve guidance channel for use in regenerating a severed nerve, comprising:

a) a tubular, biocompatible, semi-permeable membrane, said membrane having openings adapted to receive the ends of the severed nerve, and an inner lumen through which the nerve may regenerate, and b) a bioartificial three-dimensional hydrogel extracellular matrix disposed in the lumen of the semi-permeable membrane, wherein the hydrogel is derivatized throughout the matrix with a cell adhesive peptide fragment selected from the group consisting of an RGD-containing sequence comprising ArgGlyAsp; $AA_2$–$AA_4$ of SEQ ID NO: 2, a YIGSR-containing sequence comprising TyrIleGlySerArg; $AA_5$–$AA_9$ of SEQ ID NO: 1, an IKVAV-containing sequence comprising IleLysValAlaVal; $AA_{11}$–$AA_{15}$ of SEQ ID NO: 3, and a combination of any of the foregoing sequences, and wherein the average gel pore radius of the matrix is between 120 nm and 290 nm.

2. The nerve guidance channel according to claim 1 wherein the hydrogel is derivatized with the sequence CDPGYIGSR comprising CysAspProGlyTyrIleGlySerArg; SEQ ID NO:1.

3. The nerve guidance channel according to claim 1 wherein the hydrogel is derivatized with the sequence GRGDSP comprising GlyArgGlyAspSerPro; SEQ ID NO:2.

4. The nerve guidance channel according to claim 1 wherein the hydrogel is derivatized with the sequence CSRARKQAASIKVAVSADR comprising CysSerArgAlaArgLysGln AlaAlaSerIleLysValAlaValSerAlaAspArg; SEQ ID NO:3.

5. The nerve guidance channel according to any one of claims 1 and 2–4 wherein the hydrogel is a polysaccharide.

6. The nerve guidance channel according to claim 5 wherein the hydrogel is agarose.

7. The nerve guidance channel according to claim 6 wherein the agarose concentration ranges between 0.5–1.25% (w/v) and the average gel pore radius is greater than 120 nm.

8. The nerve guidance channel according to claim 6 wherein agarose concentration is approximately 1% and the average gel pore radius is approximately 150 nm.

9. A method for promoting in vivo regeneration of a severed nerve comprising securing the proximal and distal ends of the severed nerve into each end of a tubular nerve guidance channel according to any one of claims 1 and 2–8.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Cys  Asp  Pro  Gly  Tyr  Ile  Gly  Ser  Arg
    1                       5

( 2 ) INFORMATION FOR SEQ ID NO:2:

( i ) SEQUENCE CHARACTERISTICS:
        ( A ) LENGTH: 6 amino acids

```
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Gly  Arg  Gly  Asp  Ser  Pro
    1                   5

( 2 ) INFORMATION FOR SEQ ID NO:3:

( i ) SEQUENCE CHARACTERISTICS:
            ( A ) LENGTH: 19 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

Cys  Ser  Arg  Ala  Arg  Lys  Gln  Ala  Ala  Ser  Ile  Lys  Val  Ala  Val  Ser
    1                   5                             10                       15

Ala  Asp  Arg ( 2 ) INFORMATION FOR SEQ ID NO:4:

( i ) SEQUENCE CHARACTERISTICS:
            ( A ) LENGTH: 5 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

Gly  Gly  Gly  Gly  Gly
    1                   5
```